(12) United States Patent
Botti

(10) Patent No.: US 8,729,228 B2
(45) Date of Patent: May 20, 2014

(54) METHOD OF PRODUCING A MODIFIED (POLY) PEPTIDE

(75) Inventor: Paolo Botti, Vessy (CH)

(73) Assignee: University of Geneva, Geneva (CH)

( * ) Notice: Subject to any disclaimer, the term of this patent is extended or adjusted under 35 U.S.C. 154(b) by 1153 days.

(21) Appl. No.: 12/088,119

(22) PCT Filed: Sep. 28, 2006

(86) PCT No.: PCT/EP2006/009449
§ 371 (c)(1),
(2), (4) Date: Oct. 29, 2008

(87) PCT Pub. No.: WO2007/039231
PCT Pub. Date: Apr. 12, 2007

(65) Prior Publication Data
US 2009/0220452 A1     Sep. 3, 2009

(30) Foreign Application Priority Data
Sep. 28, 2005   (EP) .................... 05021189

(51) Int. Cl.
| | | |
|---|---|---|
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |

(52) U.S. Cl.
USPC ........................................... 530/333

(58) Field of Classification Search
CPC .............................. C07K 1/003; C07K 1/1077
See application file for complete search history.

(56) References Cited

FOREIGN PATENT DOCUMENTS

| WO | WO-9828434 | 7/1998 |
|---|---|---|
| WO | WO-03106615 | 12/2003 |
| WO | WO-2005014620 | 2/2005 |

OTHER PUBLICATIONS

Tsukube et al. ("Crown Ether Strategy Toward Chemical Activation of Biological Protein Functions," J. Heterocyclic Chemistry, 2001, 38, 1401-1408).*
Fraenkel-Conrat et al. ("Esterification of Proteins with Alcohols of Low Molecular Weight," J. Biol. Chem., 1945, 161, 259-268).*
Yamada, et al. 2000. "Supramolecular Complex of Cytochrome c with Lariat Ether: Solubilization, Redox Bahavior and Catalytic Activity of Cytochrome c in Methanol". Inorganic Chemistry 39(14): 3049-3056.
Oshima, et al., 2002. "Complex Formation of Cytochrome c with a Calixarene Carboxylic Acid Derivative: A Novel Solubilization Method for Biomolecules in Organic Media". Biomacromolecules 3: 438-444.

* cited by examiner

*Primary Examiner* — Marcela M Cordero Garcia
(74) *Attorney, Agent, or Firm* — Pillsbury Winthrop Shaw Pittman LLP

(57) ABSTRACT

This invention relates to a method of producing a modified (poly)peptide, said method comprising the step of modifying in an organic solvent a crown ether-bound (poly)peptide at one or more carboxylic groups by esterification or thioesterification and/or at the amino group of the N-terminal amino acid by amidation or alkylation. Furthermore provided are (poly)peptides and antibodies obtainable with the method of the invention as well as medical uses thereof.

14 Claims, 17 Drawing Sheets

Figure 1:
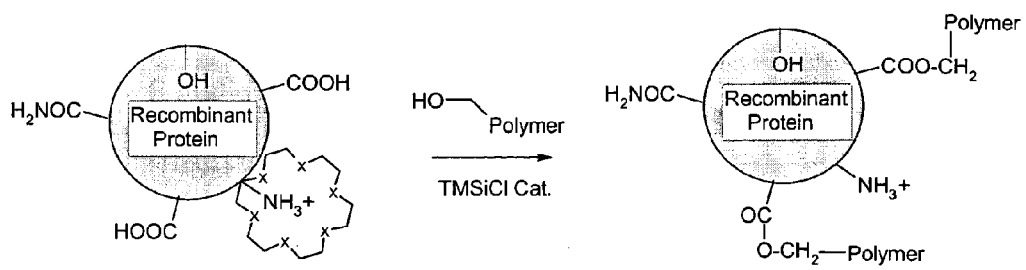
Figure 1:
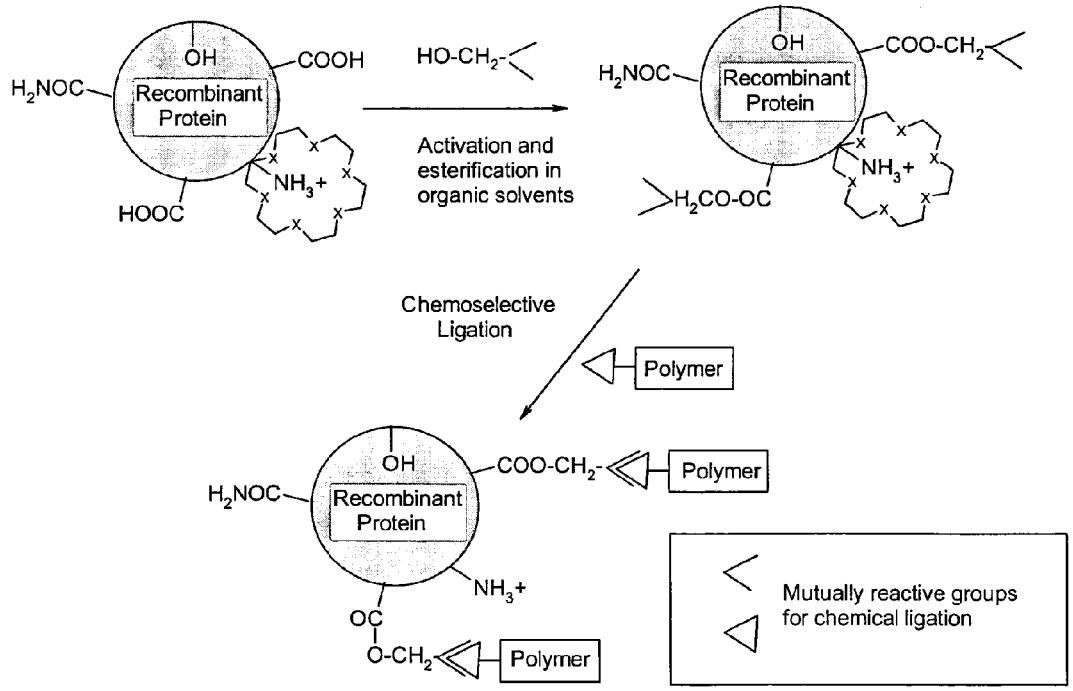

(a) Direct (One Step) Esterification Strategy (b) Modular (Two Steps) Esterification Strategy

*In vivo* regeneration of the fully active Protein

Native Fully Active Protein

Carboxy ester functionalization strategy with antibodies

Functionalization of antibodies with PTDs

(1) Esterification in organic medium
(2) Chemoselective attachment of PTDs in aqueous medium Chemoselective ligation via weak-base carbonyl compounds Unique mutually reactive functionalities Enhanced Antibody-mediated drug delivery strategy *via* new group attachment:
Example of application of drug delivery to solid tumor cells (a)

(b)

(a)

Sequence: Ac-E(OMe)-E(OMe)-E(OMe)-D-K(Rhod.)-CONH$_2$

Sequence: Ac-E(OBzl)-E(OBzl)-E(OBzl)-D(OBzl)-K(Rhod.)-CONH$_2$

Sequence: Ac-E(OMe)-E(OMe)-E(OMe)-D(OMe)-K(Ac)-CONH$_2$

Sequence: Ac-E(OBzl)-E(OBzl)-E(OBzl)-D(OBzl)-K(Ac)-CONH$_2$ (b)

1 = starting material and mono- and di-esters

2 = mono- and di-esters

3 = di- and tri-esters

SEQUENCE LISTING

```
<160> NUMBER OF SEQ ID NOS: 1

<210> SEQ ID NO 1
<211> LENGTH: 69
<212> TYPE: PRT
<213> ORGANISM: artificial sequence
```

```
<220> FEATURE:
<223> OTHER INFORMATION: model chemokine

<400> SEQUENCE: 1

Phe Ala Pro Met Ser Gln Gln Ser Thr Ser Cys Cys Phe Ala Tyr Ile
1               5                   10                  15

Ala Arg Pro Leu Pro Arg Ala His Ile Lys Glu Tyr Phe Tyr Thr Ser
                20                  25                  30

Gly Lys Cys Ser Asn Pro Ala Val Val Phe Val Thr Arg Lys Asn Arg
            35                  40                  45

Gln Val Cys Ala Asn Pro Glu Lys Lys Trp Val Arg Glu Tyr Ile Asn
    50                  55                  60

Ser Leu Glu Met Ser
65
```

METHOD OF PRODUCING A MODIFIED (POLY) PEPTIDE

This application claims priority under 35 U.S.C. § 119 of European Patent Application No. 05021189.5, filed Sep. 28, 2005, and is hereby expressly incorporated by reference in its entirety and assigned to the assignee hereof.

This invention relates to a method of producing a modified (poly)peptide, said method comprising the step of modifying in an organic solvent a crown ether-bound (poly)peptide at one or more carboxylic groups by esterification or thioesterification and/or at the amino group of the N-terminal amino acid by amidation or alkylation.

In this specification, a number of documents including patent applications and manufacturer's manuals is cited. The disclosure of these documents, while not considered relevant for the patentability of this invention, is herewith incorporated by reference in its entirety.

In the field of biomedicine, there is a need for proteins with improved pharmacological properties. To this end, therapeutic proteins have been coupled to various polymers, for example to reduce their immunogenicity, increase resistance to enzymatic degradation or prolong their half-life. For example, pegylation—the covalent derivatization of protein with polyethyleneglycol (PEG)—has been shown to improve biopharmaceutical and clinical properties of many therapeutically relevant proteins.

European patent application EP 0 809 996 describes a PEGylated derivative of interferon-α. The described conjugate has a branched PEG structure. It is obtained by conjugating the carbonyl group of a lysine residue, which in turn carries two PEG molecules linked to the α- and the ε-amino group, to an NH or an OH group of interferon-α. Lysines and also serines are explicitly mentioned as attachment sites on the protein side. Roberts et al. (2002) provide a review of peptide and protein PEGylation. Attachment sites for PEG and PEG derivatives on the protein side are $NH_2$ and to a lesser extent sulfhydryl groups. A section dedicated to reversible PEGylation mentions esters involving a PEG carboxylic acid as an intermediate. However, coupling to the protein throughout involves α- or the ε-amino groups of amino acid residues.

The chemistry known in the art to derivatize proteins with polymers often produces permanent linkages. For example, amidation and alkylation are generally permanent. Yet further, in some cases loss of activity occurs as a result of multiple derivatization. Reversibility of amidation may only be achieved when a protecting group for the amino group is used to carry the molecule to be attached to the protein (Tsubery et al. (2004)).

In medicinal chemistry, esterification has been used to obtain a drug retard form (e.g. cortisone retard forms) and esterification with lipophilic alcohols to achieve enhanced absorption (e.g. penicillin esters such as pivampicillin and talampicillin). In the first case, the key effect is that the esterified drug or prodrug is inactive. The active form is then slowly released by the ester hydrolysis. In the second case, the relevant effects of esterification are the removal of the charge of the carboxylate and the enhanced lipophilicity resulting from the lipophilic alcohol part of the ester. However, the methods employed for cortisone and penicillin modification are not transferable to the modification of proteins.

Peptide and protein lipidation is used to obtain improved mucosa permeation (enhanced absorption and delivery), to improve the bioavailability and in some cases produced enhanced potency (Wang, J. et al., *Pharm Res.* 19, 609-14 (2002); Hartley, O. et al., *PNAS,* 101, 16460-16465 (2004)).

However, protein lipidation with standard methods is generally permanent (not reversible) and often (when amide or urethane bonds are produced) causes protein precipitation. Furthermore lipids are generally poorly soluble in water and it is difficult to functionalize a protein in a reproducible and controllable manner with lipids.

Yamada et al. (2000) describes the use of lariat ethers (or crown ethers) for the solubilization of cytochrome c in methanol. The authors investigate the effect of the derivatization of crown ethers on the solubilization efficiency for cytochrome c. The purpose of solubilization is the provision of cytochrome c dissolved in organic solvent, noting that the authors aim is the provision of effective biocatalysts working in organic solvents. Oshima et al. (2002) study calixarene derivatives as a recognition tool for biopolymers. They investigate the selectivity of various calixarenes in the extraction of lysine-rich proteins. A particular calixarene is employed for the selective extraction of cytochrome c. Cytochrome c dissolved in chloroform is described to exhibit the uncommon activity of a peroxidase. Both papers (i) explore the effect of chemical modification of the solubilizing agent on solubilization efficiency and (ii) report the observation of uncommon catalytic properties of the solubilized protein. Julian et al. (2001) also describe cytochrome c solubilized in organic solvents by crown ethers. Using ESI-MS, data are provided indicating that four 18-crown-6 molecules strongly bound exposed lysine side-chains on the protein surface. A derivatization of the protein, once solubilized, is neither envisaged nor suggested in these publications.

Botti et al. (1996) describe the stepwise synthesis of peptides from smaller peptides wherein crown ethers are used as protection groups. As necessary requirements for the success of their method, Botti et al. mention the N-terminal residues having either a secondary nitrogen (such as Pro) or being doubly substituted at the nitrogen atom (such as Fmoc-protected amino acids or peptides). Furthermore, the carboxyl functions of Asp and Glu have to be protected. The intention of Botti et al. (1996) was the provision of a method of synthesizing peptides, wherein crown ethers are used as non-covalent protection groups as opposed to the covalent protection/de-protection strategy commonly used in peptide synthesis.

There is an unmet need for a methodology which permits the safe attachment of polymers, i.e. without adverse effects on protein activity, in a controlled manner which furthermore yields a linkage which is fully reversible in vivo. In view of the limitations of the methods described in the prior art, the technical problem underlying the present invention was therefore the provision of improved or alternative means and methods for the modification of the pharmacological properties of proteins.

Accordingly, this invention relates to a method of producing a modified (poly)peptide, said method comprising the step of modifying in an organic solvent a crown ether-bound (poly)peptide at one or more carboxylic groups by esterification or thioesterification and/or at the amino group of the N-terminal amino acid by amidation or alkylation.

The term "(poly)peptide" as used herein describes peptides, consisting of up to 30 amino acids, and polypeptides, consisting of more than 30 amino acids. It is understood to comprise proteins, fragments of proteins and synthetic molecules. It furthermore comprises antibodies as well as fragments and derivatives of antibodies.

The term "modified (poly)peptide" according to the invention relates to derivatization by (thio)esterification of carboxyl groups and/or amidation or alkylation of the amino group of the N-terminal amino acid.

The term "organic solvent" is known in the art and relates to non-aqueous solvents used in organic synthesis. Generally speaking, organic solvents are more lipophilic or hydrophobic than water. As a consequence, their logP values are generally greater than zero. The logP value is the decadic logarithm of the partition coefficient P which in turn is defined as the ratio $P=[A]_{n\text{-}octanol}/[A]_{water}$, wherein A is the chemical species considered, in this case the organic solvent. Organic solvents according to the invention include methanol, ethanol, alcohols from $C_3$ to $C_{10}$, acetonitril, butanone, 1,1,1-trifluoroethane (TFE), hexafluoroisopropanol (HFIP), ethyl acetate, carbon tetrachloride, butanol, dibutyl ether, diethyl ether, cyclohexane, methylene chloride (dichloromethane), hexane, butyl acetate, di-isopropyl ether, benzene, dipentyl ether, chloroform, heptane, tetrachloroethylene, toluene, hexadecane, dimethylformamide (DMF), tetrahydrofurane (THF) and dioxane.

The term "crown ether" is well known in the art and designates (macro)cyclic polyethers assuming a crown-shaped conformation. The commonly used nomenclature is n-crown-m, wherein n designates the total number of atoms in the ring and m designates the number of oxygen atoms in the polyether ring. The term includes derivatives wherein one or more aromatic rings have been condensed with the (macro)cyclic ring, for example dibenzo-18-crown-6.

As (poly)peptides are generally insoluble in organic solvents, protein derivatization, for example with biocompatible polymers such as PEG or with lipids, is currently limited to the type of reactions that do not require organic solvents. Complexation of (poly)peptides with crown ethers permits the preparation of solutions of said (poly)peptides in organic solvents which in turn open the possibility to perform chemical modifications which can not be effected in aqueous solution, in particular not with an unprotected (poly)peptide. This is of particular relevance for the chemical modification of water-soluble proteins and/or for the modification of the (poly)peptides with molecules which are not water-soluble or not to a sufficient extent such as lipids. Surprisingly and advantageously, said complexation with crown ethers occurs with the charged primary amino groups (Lys and Arg side-chains, and the N-terminal amino group) on the surface of the (poly)peptide. As a consequence, usually no misfolding of the protein occurs—neither as a result of the complexation nor upon the transfer to the organic solvent—and the biological activity does not get lost. For example, PSC-Rantes [N-formyl-Trp$^{57}$], an anti-HIV-1 protein, fully maintained its antiviral activity upon complexation with crown ethers (and subsequent dissolution in organic solvents) (see the Examples enclosed herewith). Concomitantly, the complex formed between (poly)peptide and crown ether molecule(s) is sufficiently hydrophobic—the charged amino groups are masked by the crown ether—to confer solubility in organic solvents. Masking of amino groups also serves for protecting them from undergoing side reactions. Complexation with crown ethers can be performed under mild conditions and therefore may be effected using fully unprotected (poly)peptides. The complexation with crown ethers is reversible and can be fine-tuned, for example by changing the pH or by addition of simple salts such as sodium chloride (NaCl).

Ester bonds and thioester bonds have the distinct advantage that they are reversible in vivo. Cleavage occurs by (i) uncatalysed hydrolysis and/or (ii) enzymatic cleavage by esterases (see FIG. 2 for an illustration of these cleavage processes occurring on a modified (poly)peptide obtained via the "indirect" method (see below) according to the invention). Thioesters may be cleaved in vivo by a third mechanism, viz. via thiol exchange with endogenous thiols (for example glutathione). The rate of all types of cleavage depends on the structure of the substrate. By choosing appropriately the moiety to be attached via an ester or thioester bond to the (poly)peptide, a tailored release rate may be achieved. Esterification of the (poly)peptide carboxylic groups has the advantage that—and opposed to the prior art reviewed herein above—amino groups remain unchanged, i.e., their charges are not suppressed as a consequence of derivatization, thereby avoiding misfolding and/or loss of solubility followed by precipitation of the (poly)peptide. However, esterification on carboxyl groups of (poly)peptides has to be carried out in an organic solvent that contains an excess of hydroxyl groups (alcohol). Noting that esterification or thioesterification of the (poly)peptide carboxyl groups is a desirable route of modifying said (poly)peptide, the present inventors surprisingly found out that a crown ether-bound form of the (poly)peptide is a particularly suitable intermediate for carrying said esterification. Since the (poly)peptide maintains or essentially maintains its native structure upon complexation with crown ether and transfer into an organic solvent, esterification is likely to occur only on the surface-exposed carboxyl groups.

By using the method of the invention, (poly)peptides with enhanced pharmacological and/or pharmacokinetic properties may be obtained. Said enhanced properties include enhanced absorption or delivery, protection from degradation, prolonged activity and/or increased potency (for further details see below). At the same time, and as discussed above, while the modified form of the (poly)peptide ensures said enhanced properties, it is the reversibility of the modifications effected with the method of the invention which ensures that the unmodified (poly)peptide is eventually set free and exerts its biological/therapeutic effects. Alternatively, the (poly)peptide in its modified form as obtained by the method of the invention may be capable of exerting therapeutic effects of interest and different from those of the unmodified (poly)peptide. Yet further, a therapeutically relevant form of the (poly)peptide may be formed upon partial hydrolysis, cleavage and/or thiol exchange such that some of the modifications are still present in the therapeutically relevant form while others are not.

If the organic solvent bears an hydroxyl moiety (alcohol), the addition of an activating agent allows mild and controllable ester or thioester formation. Mild conditions include reaction at room temperature. A list of suitable activating agents can be found in: T. W. Green and P. G. M. Wuts, *Protecting Group in Organic Synthesis*, III Ed, 1999, John Wiley & Sons New York 373-377 and includes silanes or silylating agents such as trimethylchlorosilane (TMSiCl), carbodiimides (for example DIC, DCU), 1,1-carbonyldiimidazole (CDI), 2-ethoxy-1-(ethoxycarbonyl)-1,2-dihydroquinoline (EEDQ), and trialkyl phosphites and acetals of dimethylformamide. The term "controllable" refers to an adjustable degree of functionalization (by ester and/or thioester formation). Adjustment is effected by the excess of activating agent used. An overview of esterification reactions and mechanisms is provided in J. March, *Advanced Organic Chemistry*, 4$^{th}$ ed. Wiley & Sons 1992, pp. 392-400.

Figure 13:
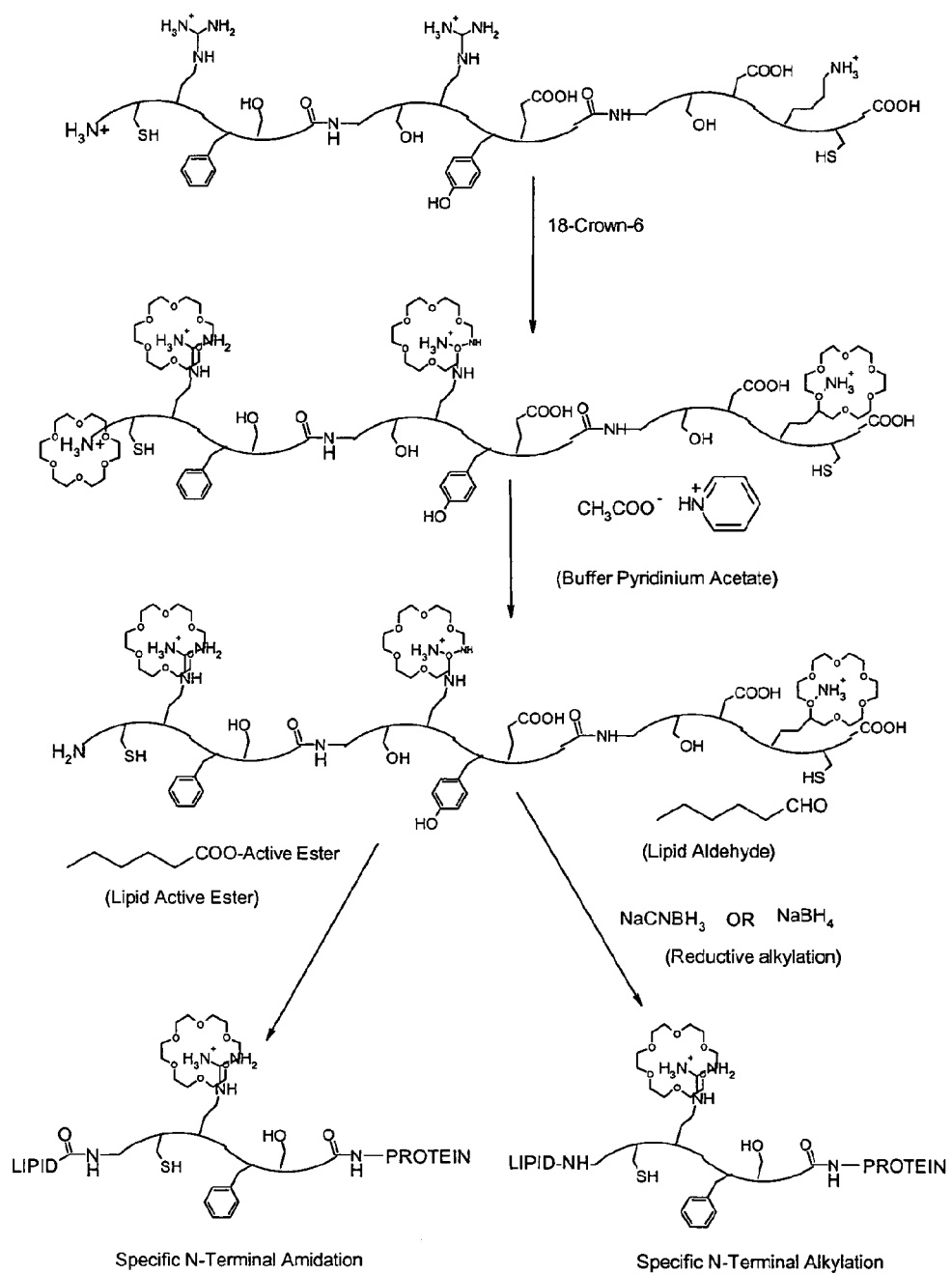

Selective modification of the amino group of the N-terminal amino acid, wherein side-chain amino groups of the basic amino acids are not modified, may be achieved by the use of appropriate organic buffers such as pyridinium acetate which establishes a pH equivalent of mildly acidic conditions, preferably in a pH range of about 4 to about 6. Under such conditions the side chain amino groups will remain substantially protonated and protected by the crown ether, whereas the amino group of the N-terminal amino acid, being less basic as compared to the side chain amino groups, is not or not completely protonated, therefore not or not completely protected by the crown ether and accordingly available for reaction. Preferred groups to be attached to the amino group of the N-terminal amino acid include lipids and biocompatible polymers. The terms "lipid" and "biocompatible polymer" are defined herein below as are preferred embodiments of these groups. Said groups to be attached are preferably provided as activated esters such as fatty acid activated esters or aldehydes. Reaction of the activated ester with the free N-terminal amino group yields an N-terminally amidated (poly) peptide; and reaction of the aldehyde under reducing conditions (e.g. NaCNBH$_3$ or NaBH$_4$) gives a (poly)peptide with an alkylated amino group of the N-terminal amino acid. FIG. 13 provides exemplary reaction sequences for N-terminal modifications. Alternatively, amidation of the amino group of the N-terminal amino acid may be done with one amino acid or a oligopeptide consisting of 2, 3, 4, 5, or up to about 10 amino acids, wherein said amino acid or at least one of the amino acids constituting said oligopeptide are selected from a non-naturally occurring amino acid, a D-amino acid, an amino acid derivative or a combination thereof. The term "non-naturally occurring amino acid" relates to the general non-occurrence in proteins. The term comprises β-alanine, α-aminobutyric acid, γ-aminobutyric acid, α-aminoisobutyric acid, norvaline, norleucine, ε-lysine, ornithine, homoserine and hydroxyproline. The term "D-amino acid" is understood to comprise the D-counterparts of both naturally occurring amino acids as well as of non-naturally occurring amino acids. The term "amino acid derivative" includes amino acids with protected side chains and N-alkylated amino acids. Suitable protection groups are well known in the art. In this embodiment, a (poly)peptide, which could be produced recombinantly, could be modified by the method of the invention at its N-terminus to obtain a (poly)peptide with modified or enhanced pharmacological and/or pharmacokinetic properties. The added amino acid or at least one of the amino acids constituting said oligopeptide may be amino acids which are not coded by the gene or mRNA encoding the (poly)peptide.

In a preferred embodiment of the method of the invention, the modifying by an ester or thioester bond is selected from the group consisting of the formation of an ester or thioester bond with one or more (a) biocompatible polymers; (b) lipids; (c) linker molecules comprising a hydroxyl group or sulfhydryl group; (d) side-chain hydroxyl groups of said (poly) peptide; (e) oligonucleotides; (f) (pro)drugs; (g) markers; (h) labels; (i) molecules of methanol or benzyl alcohol; (j) small molecules having a cognate transport carrier; and any combination of (a) to (j).

This embodiment relates to a way of attaching the recited molecules or groups to said (poly)peptide which requires the molecule or group to be attached to the (poly)peptide (to be modified by said attachment) to bear at least one hydroxyl group (see FIG. 1a for illustration). This embodiment is also referred to as a "direct" (or "one step") modification as opposed to the alternative or additional attachment via the "indirect" way involving said linker, said indirect way being further detailed below.

The term "biocompatible polymer" refers to polymers which do not give rise to adverse reactions of the human or animal body. Biocompatible polymers are widely used for prosthetic purposes, for sutures, for sustained and/or delayed release pharmaceutical compositions and the like. The term "polymer" is understood to comprise both polymers in the narrow sense, i.e. molecules formed from a plurality of building blocks or one or more than one type (in the latter case said polymers are also referred to as co-polymers), wherein upon formation of the polymer from the building blocks no further molecule(s) such as water is formed, as well as polycondensates, i.e. polymers according to the present invention, wherein upon formation of the polymer from its building blocks (a) further molecule(s) such as water is/are formed in addition to the polymer. For those embodiments, where said biocompatible polymer is to be used in the "direct" method of the invention, it is understood that the biocompatible polymer exhibits at least one free hydroxyl or free sulfhydryl group.

The term "lipid" is well known in the art and relates to predominantly lipophilic/hydrophobic molecules which may carry a polar headgroup, thereby rendering the lipid molecule amphiphilic. For a use of lipids in the direct method of (poly) peptide modification, the presence of a hydroxyl group is a prerequisite. Lipids according to the invention include simple lipids such as hydrocarbons (triacontane, squalene, carotinoids), alcohols (wax alcohol, retinol, cholesterol, linear mono- or polyhydroxylated hydrocarbons, preferably with two to about 30 carbon atoms), ethers, fatty acids and esters such as mono-, di- and triacylglycerols. Furthermore included are complex lipids such as lipoproteins, phospholipids and glycolipids. Phospholipids in turn comprise glycerophospholipids such as phosphatidic acid, lysophosphatidic acid, phosphatidylgylcerol, cardiolipin, lysobisphosphatidic acid, phosphatidylcholine, lysophosphatidylcholine, phosphatidylethanolamine, phosphatidylserine, phosphatidylinositol and phosphonolipids. Glycolipids include glycoglycerolipids such as mono- and digalactosyldiacylgylcerols and sulfoquinovosyldiacylgylcerol. Also included by the term "lipid" according to the present invention are sphingomyelin glycosphingolipids and ceramides.

It is understood that the term "linker molecule" relates to moieties which are capable of linking at least two molecular entities together. For the purpose of performing the linking, said linker molecule, in addition to the above mentioned hydroxyl group or sulfhydryl group, comprises another functionality which is either in protected or free form, wherein said functionality is amenable to chemical reaction, preferably a chemoselective reaction. Said chemoselective reaction preferably involves only a reaction between said functionality and a second molecule (said modified (poly)peptide or (poly) peptide to be modified being the first molecule) with the first molecule not participating in said chemoselective reaction. Preferred linkers comprise or consist of a hydrocarbon chain with two to about 15 carbon atoms, said hydroxyl group or sulfhydryl group and said (second) functionality. Preferred structures of said functionality are provided herein below and in FIG. 5.

Esterification with side-chain hydroxyl groups of said (poly)peptide refer to the formation of internal ester bonds within the same (poly)peptide molecule which is to be modified. Hydroxyl groups may be provided by the side-chains of Ser, Thr or Tyr. The resulting esters (lactones) are cyclic or macrocyclic.

The term "oligonucleotide" according to the invention comprises in addition to oligoribo- and oligodeoxyribonucleotides molecules with substantially the same binding properties, but a different backbone, e.g. a peptidic backbone instead of the phosphate-sugar backbone. Accordingly, the term "oligonucleotide" comprises peptide-nucleic acids (PNAs) as well as oligonucleotide-PNA chimeras.

The term "PNA" stands for "peptide nucleic acid". In brief, a PNA is a synthetic DNA-mimic with an amide backbone in place of the sugar-phosphate backbone of DNA or RNA (Nielsen et al. (1991) Science, 254, 1497-1500; Egholm et al. (1993), Nature, 365, 566-568). PNAs exhibit several advantageous features. They are stable under acidic conditions and resistant to nucleases as well as proteases (Demidov et al. (1994), Biochem. Pharmacol., 48, 1310-1313). Their electrostatically neutral backbone increases the binding strength to complementary DNA as compared to the stability of the corresponding DNA-DNA duplex (Wittung et al. (1994), Nature 368, 561-563; Ray and Norden (2000), Faseb J., 14, 1041-1060). Thus, PNA oligomers can be shorter than oligonucleotides when used as hybridisation probes. On the other hand, mismatches have a more destabilising effect, thus improving discrimination between perfect matches and mismatches. For its uncharged nature, PNA also permits the hybridisation of DNA samples at low salt or no-salt conditions, since no inter-strand repulsion as between two negatively charged DNA strands needs to be counteracted. As a consequence, the target DNA has fewer secondary structures under hybridisation conditions and is more accessible to probe molecules. PNA chimera according to the present invention are molecules comprising one or more PNA portions. The remainder of the chimeric molecule may comprise one or more DNA portions.

Preferred lengths of the oligonucleotides of the invention are between 12 and 200 bases, more preferred between 20 and 100. In those embodiments where the oligonucleotide of the invention is an siRNA, a duplex with strands of lengths between 20 and 25 bases, in particular between 21 and 23 bases is preferred as is a 3' overhang. Most preferred for the purpose of RNAi are siRNA duplexes composed of 21-nt sense and 21-nt antisense strands, paired in a manner to have a 19-nucleotide duplex region and a 2-nucleotide overhang at each 3'-terminus.

The term "(pro)drug" is understood to comprise both drugs and prodrugs. The term "drug" comprises any active agent approved for human or veterinary application (for listings see, for example, the Merck Index, 13$^{th}$ ed. Merck Publishing Group, Rahway, N.J., USA; and Martindale, "The Complete Drug Reference" London: Pharmaceutical Press. Electronic version, Thomson Micromedex, Greenwood Village, Colo., 34$^{th}$ ed.). A "prodrug" is a compound that is generally not biologically and/or pharmacologically active. However, when activated, typically in vivo by enzymatic or hydrolytic cleavage to convert the prodrug to a biologically and/or pharmacologically compound (drug), the administration of the prodrug will have the intended medical effect. Prodrugs are typically formed by chemical modification of biologically and/or pharmacologically compound. Conventional procedures for the selection and preparation of suitable prodrug derivatives are described, for example, in Design of Prodrugs, ed. H. Bundgaard, Elsevier, 1985. Prodrugs are useful for example when the active drug may be too toxic to be administered systemically, the active drug is absorbed poorly by the digestive tract, or the body breaks down the active drug before it reaches its target. Activation of a prodrug may occur by metabolization in the body, for example after passing intracorporal barriers such as the cell membrane.

The term "marker" relates to molecules, fragments or radicals which facilitate or permit detection of the modified (poly) peptide. Markers include proteinaceous molecules such as fluorescent proteins including blue, cyan, green and yellow fluorescent protein (BFP, CFP, GFP and YFP) and luminescent proteins. Also included are reporter constructs well known in the art.

The term "label" is well known in the art and includes a molecule, fragment or radical bearing a radioactive, fluorescent and/or luminescent etc. atom or functional group. Radioactive nuclides include $^{32}$P, $^{35}$S, $^{3}$H, $^{90}$Y and $^{131}$I. Fluorescent labels include fluorenes, pyrenes, xanthenes including fluoresceins, rhodamines, coumarins, naphthylamines, acridines, benzoxazoles, benzodioxazoles, stilbenes, poly(p-phenylene vinylene)s, polythiophenes, poly(phenylene ethynylene)s and poly(para-phenylene)s. Naphthylamines may have the amino group in the alpha or beta position and include 1-dimethylaminonaphthyl-5-sulfonate, 1-anilino-8-naphthalene sulfonate and 2-p-toluidinyl-6-naphthalene sulfonate. Coumarins include 3-phenyl-7-isocyanatocoumarin; acridines include 9-isothiocyanatoacridine and acridine orange; and benzoxazoles include N-(p-(2-benzoxazolyl)phenyl)maleimide.

It is understood that the use of the plural form, such as "fluorenes", indicates that not only fluorene itself, but also derivatives thereof known in the art at the priority date of the instant application are embraced.

Specific fluorescent labels according to the invention include the following commercially available (for example from Synthegen) fluorescent dyes: Tamra-dT, 5-Fluorescein (FITC), 5-Carboxyfluorescein (FAM), 6-Carboxyfluorescein (FAM), 3' 6-Carboxyfluorescein (FAM), 6-Carboxyfluorescein-DMT (FAM-X), 5(6)-Carboxyfluorescein (FAM), 6-Hexachlorofluorescein (HEX), 6-Tetrachlorofluorescein (TET), JOE, LightCycler Red 640, LightCycler Red 705, FAR-Fuchsia (5'-Amidite), FAR-Fuchsia (SE), FAR-Blue (5'-Amidite), FAR-Blue (SE), FAR-Green One (SE), FAR-Green Two (SE), Oregon Green 488, Oregon Green 500, Oregon Green 514, BODIPY FL-X, BODIPY FL, BODIPY-TMR-X, BODIPY R6G, BODIPY 650/665, BODIPY 564/570, BODIPY 581/591, BODIPY TR-X, BODIPY 630/650, BODIPY 493/503, Carboxyrhodamine 6G, MAX, 5(6)-Carboxytetramethylrhodamine (TAMRA), 6-Carboxytetramethylrhodamine (TAMRA), 5(6)-Carboxy-X, Rhodamine (ROX), 6-Carboxy-X-Rhodamine (ROX), AMCA-X (Coumarin), Texas Red-X, Rhodamine Red-X, Marina Blue, Pacific Blue, Rhodamine Green-X, 7-diethylaminocoumarin-3-carboxylic acid, 7-methoxycoumarin-3-carboxylic acid, Cy3, Cy3B, Cy5, Cy5.5, DY-505, DY-550, DY-555, DY-610, DY-630, DY-633, DY-636, DY-650, DY-675, DY-676, DY-681, DY-700, DY-701, DY-730, DY-750, DY-751, DY-782, Cy3.5 and EDANS.

The term "small molecule having a cognate transport carrier" designates molecules which are recognised and transported by specific transport carriers in the body. Such molecules are well known in the art as are their cognate transport carriers. Preferred molecules include vitamin $B_{12}$ (see Russell-Jones, G. J., Adv. Drug. Deliv. Rev., 2001, 46, 59-73) and vitamin C.

In a further preferred embodiment of the method of the invention, said carboxylic group is selected from the group consisting of (a) one or more side-chain carboxylic groups of Glu; (b) one or more side-chain carboxylic groups of Asp; (c) the main-chain carboxylic group of the C-terminal amino acid; and (d) any combination of (a) to (c).

In a further preferred embodiment, said method comprises the further step of reacting said linker with a molecule selected from the group consisting of one or more (a) biocompatible polymers; (b) lipids; (c) linkers; (d) second (poly) peptides; (e) oligonucleotides; (f) (pro)drugs; (g) markers; (h) labels; (i) small molecules having a cognate transport carrier; and any combination of (a) to (i).

This embodiment relates to a modular method of producing a modified (poly)peptide according to the invention (also referred to as "indirect" or "two step" method herein). In this embodiment, the (poly)peptide is esterified in a first step with a linker bearing a hydroxyl group or sulfhydryl group, wherein said linker furthermore bears a second functionality that introduces a "hook" at each ester bond formed. Thus, after the first step, a defined number of ester bonds are generated, and the group of choice can be attached in a second step via a smooth chemoselective reaction through said second functionality (see FIG. 1b for illustration). In such way we can fine-tune the level of functionalization of the group that is to be linked to the protein. This technique is ideal for the insertion of large groups such as polymers or hydrophobic groups like lipids to obtain a retard form of a therapeutically relevant (poly)peptide. The chemoselective reaction (the second step) is adjusted such as to achieve in each case a desired level of substitution. Finally with the modular strategy it is possible to functionalize the (poly)peptide of interest with more than one type of group to further enhance the biopharmaceutical properties.

In a preferred embodiment, said further step of reacting said linker is effected via weak base-carbonyl chemistry. Such reaction can be performed under very mild, weakly acidic conditions. Therefore, the structure of the (poly)peptide or antibody or fragment or derivative thereof is not interfered with. Preferably, said reacting comprises reacting an electrophilic group such as an aldehyde or ketone with a nucleophilic group such hydrazine or hydroxylamine derivatives with the general formula $NH_2NHR$ or $NH_2OR$, respectively or a 1,2-functional group to generate an etherocyclic ring as reaction product. Preferred 1,2-functional groups are 1,2-amino-thiol, 1,2-amino-hydroxy, 1,2-hydroxy-thiol, 1,2-dithiol and 1,2-dihydroxy. The nucleophilic group may be said second functionality of said linker in which case the group to be attached to the linker bears an electrophilic group or vice versa (see FIG. 5).

In another preferred embodiment, the copper-catalyzed coupling of alkyne and azide groups (generically named click chemistry, see for example V. Rostovtsev et. Al. 2002, Angew. Chem., 41, 2596) is used for chemoselectively linking the linker to the molecule to be attached. Attachment occurs via etherocyclic ring formation.

Figure 8:
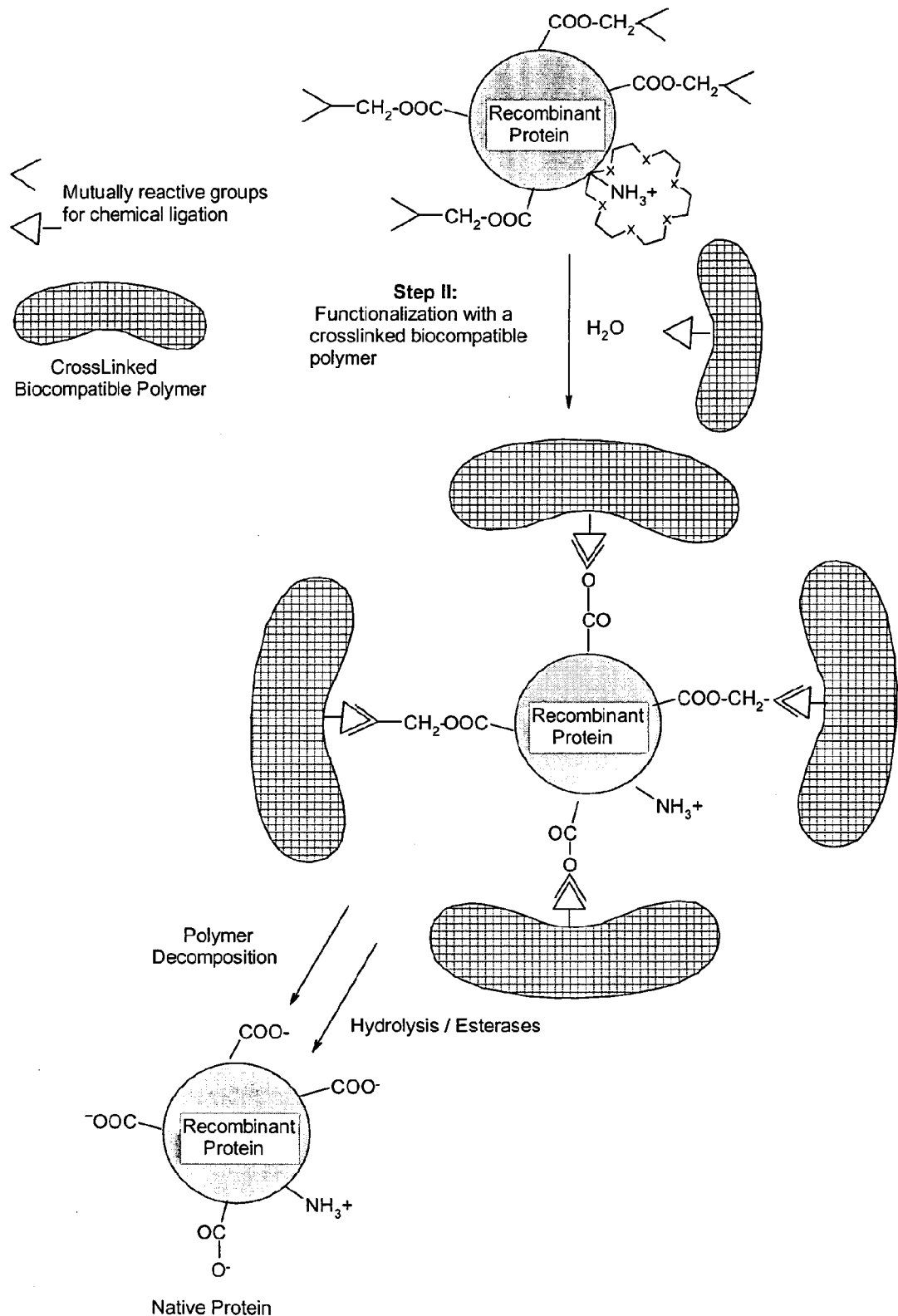
Figure 9:
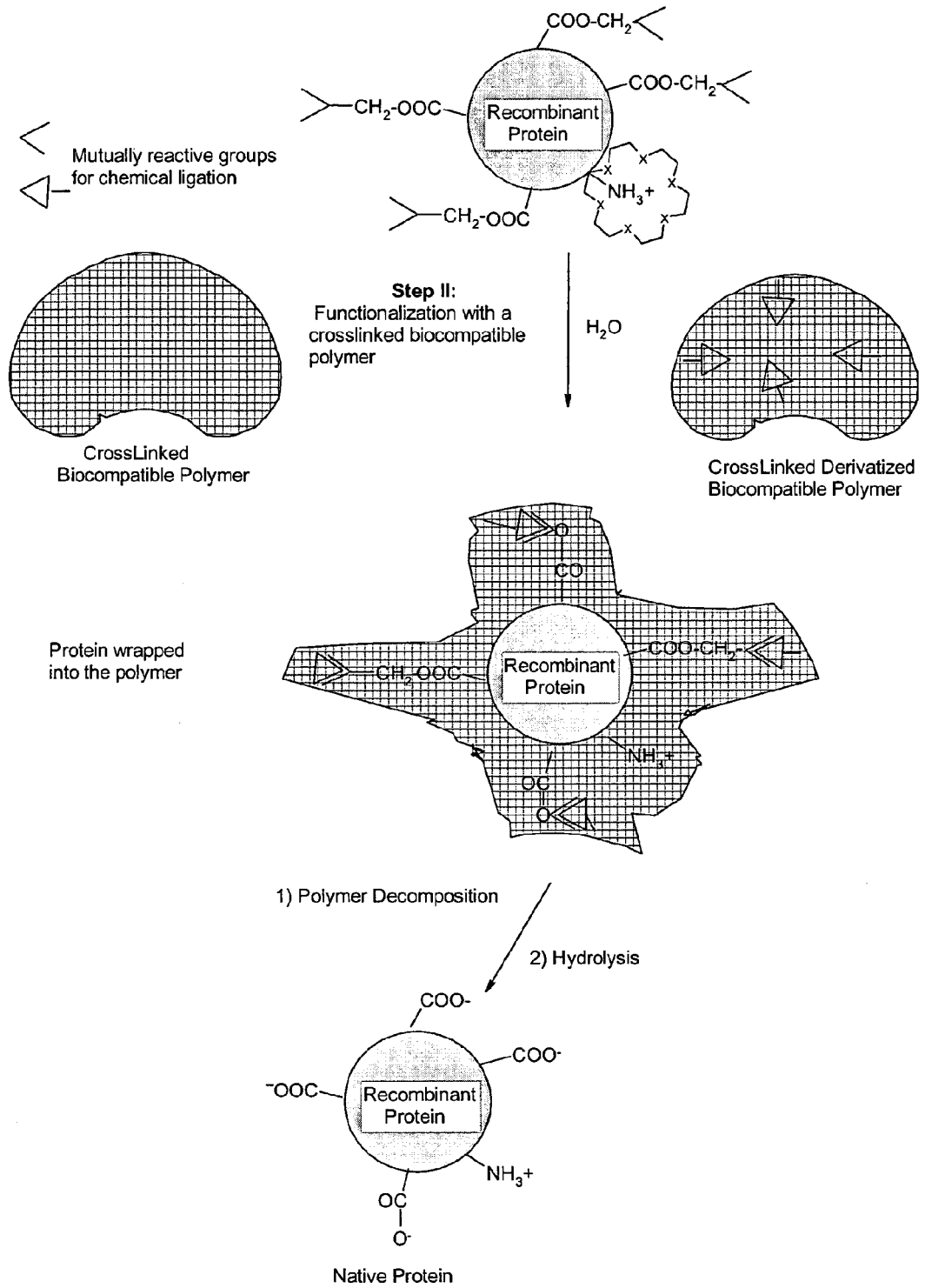

As a consequence of the structural modification of the (poly)peptide by the attachment of a biocompatible polymer, the modified (poly)peptide obtained thereby exhibits one or more of the following surprising and/or advantageous functional properties: (i) enhanced absorption or delivery, (ii) protection from degradation, (iii) prolonged activity, and (iv) increased potency. Enhanced absorption or delivery results from the biocompatible polymer being preferentially absorbed or translocated, for example across the cell membrane or intracorporal barriers such as the blood brain barrier or mucosal surfaces, for example such that the absorption or translocation of said biocompatible polymer precedes and facilitates the absorption or translocation or the (poly)peptide. Said biocompatible polymer may be linear (see illustration in FIG. 7), branched or cross-linked (see FIGS. 8 and 9). Enhanced absorption may be achieved either by derivatizing with linear or with branched or cross-linked biocompatible polymers. Protection from degradation, e.g. by enzymes, is achieved by a shielding effect of the biocompatible polymer attached to the (poly)peptide. In this case, branched or cross-linked polymers are preferred (see FIGS. 8 and 9). FIG. 8 illustrates partial shielding, which preferably is accomplished by derivatizing the (poly)peptide with biocompatible polymer molecules which are smaller than the (poly)peptide, whereas FIG. 9 illustrates complete shielding, which preferably is accomplished with polymer molecules larger than the (poly)peptide, e.g. about two times as large with regard to molecular weight or overall size.

Similarly, said shielding effect may entail prolonged activity, since in order to exhibit biological activity, biocompatible polymer has to be at least partially degraded or the (poly)peptide completely released. Modified (poly)peptides according to the invention exhibiting such prolonged activity are useful, for example, as retard formulations of said (poly)peptide. Increased potency has been reported for lipidated (poly)peptides. Without being bound by a specific theory, this effect is envisaged to be due to the enhanced lipophilicity of the (poly)peptide that allows adhesion to the cell-membrane and enhanced or prolonged interaction with the cognate receptor.

In a preferred embodiment, the reacting of said linker with one or more of the above recited molecules is effected in aqueous medium. In other words, upon completion of the first step of the two-step method of the invention, the (poly)peptide modified with one or more linkers may be transferred to an aqueous medium where the second step, i.e., the derivatization of the linker, is to be performed. The term "aqueous medium" comprises water, buffers and solutions in general wherein water is used as solvent. Alternatively, in cases where the group or molecule to be attached to said linker requires organic solvent for solubility reasons, the derivatized (poly)peptide is complexed with crown ether and an organic solvent according to the invention or mixtures of aqueous medium and organic solvent may be used.

In a preferred embodiment of the method of the invention, said biocompatible polymer is selected from the group consisting of polyethers, polysaccharides, polyesters (including polyorthoesters), polyalkylcyanoacrylates, hydroxyalkylacrylamides, surfactants and mixtures thereof.

The term "surfactant" is well known in the art. It is understood that it comprises molecules capable of forming micelles. The term "surfactant" not only includes molecules of polymeric nature but also lipids, for example phospholipids and glycolipids further detailed herein above.

With regard to its physicochemical properties, a biocompatible polymer according to the invention may be a hydrogel. Alternatively or additionally, said biocompatible polymer may be a surfactant or tensioactive. Also alternatively or additionally, said polymer(s) may be capable of forming liposomes, polymeric micelles, microspheres, microcapsules and/or nanoparticles. By using the method of the invention, a crown ether-bound (poly)peptide may be covalently linked to a polymer which is either the only constituent or one of the constituting molecules of the liposome, micelle, microsphere, microcapsule or nanoparticle. Thereby a liposome, micelle, microsphere, microcapsule or nanoparticle is obtained which contains a covalently linked (poly)peptide in its internal. Crown ethers trapped in the liposome, micelle, microsphere, microcapsule or nanoparticle may be removed by washing, for example with aqueous solution of sodium chloride.

Preferred polysaccharides include cyclodextrins, starch, chitin, chitosan, xanthan, dextrans, cellulose, alginates, pullulan, pectine, glycolipids and glycosaminoglycans (including chondroitin sulfates, dermatan sulfate, keratan sulfate, heparan sulfate, heparin and hyaluronic acid).

In a more preferred embodiment, said polyester is polymer or co-polymer wherein the building block (or at least one of the building blocks in case of a co-polymer) is an α-hydroxy acid such as lactic acid or glycolic acid.

In a further preferred embodiment, said biocompatible polymer is branched and/or cross-linked.

Branched and/or cross-linked polymers are particularly suitable for the above described shielding effect, i.e., the wrapping of the (poly)peptide.

Preferably, the polyether is polyethylene glycol (PEG) or the polyester is poly(lactic/glycolic) acid. The term "PEG" relates to a class of polyether polyols well known in the art.

PEG is available from commercial suppliers in a broad range of molecular weights. An exemplary molecular weight range is from about 100 to about 10000000, including PEG with a molecule weight of about, for example, 200, 300, 400, 500, 800, 1000, 2000, 5000, 10000, 100000, 500000 and 1000000. The term "poly(lactic/glycolic) acid" according to the invention comprises polylactic acid, polyglycolic acid and copolymers of lactic and glycolic acid.

Preferably, said second (poly)peptide is a membrane-penetrating (poly)peptide. In many cases, cell delivery can be achieved by the incorporation into the target protein of protein transduction domains (or protein transducing domains; PTDs). These generally short to medium size polypeptide sequences, for this reason often called cell-penetrating (poly) peptides (CPPs) or membrane-penetrating (poly)peptides, do not exhibit marked lipophilicity, but are amphipathic and generally carry a number of positive charges at physiological pH. They are able to efficiently cross the plasma membrane of cells, either alone, or linked to protein 'cargo'. Although the mechanism by which they cross membranes has yet to be fully elucidated, PTDs are being increasingly used as vectors for delivering proteins to cells and show potentials for their application in drug delivery. Thus, and without being bound by a specific theory it is envisaged that the derivatization of a protein with polymers via ester formation not only enhances the protein lipophilicity per se by elimination of negative charges and the addition of the lipophilic polymer, but also renders the chemical-physical properties of the proteins similar to the cationic CPP, thereby permitting cell permeation.

In a preferred embodiment, said membrane-penetrating (poly)peptide is selected from the group consisting of Penetratin (Antennopedia 43-58), TaT, TAT 46-60, PTD-4, SynB1 and SynB3 (Protegrin I), Transportan, MAP (Model Amphipatic peptide), Pep-1, Proline rich peptide (VXLPPP)$_n$, pVEC, pISL, polyArginine, SN50, MPG (see Zorko, M and Langel, U. (2005) Advanced Drug Delivery Reviews; 57: 529-545). The above mentioned membrane-penetrating peptides can be in the natural form (formed by L-residues), or formed by D-residues.

In another preferred embodiment the second (poly)peptide is a protein or (poly)peptide which is recognized and transported by gastro-intestinal (GI) transport carriers. Such (poly)peptides and their cognate transport carriers in the body are well known in the art. Preferred (poly)peptides which are recognized and transported by gastro-intestinal transport carriers are transferrin (Xia, C. Q. et al. J. Pharmacol. Exp. Ther., 2000, 295, 594-600) and lectins (Lehr, C. M., J. Control. Rel., 2000, 65, 19-29).

In a preferred embodiment of the method of the invention where a second (poly)peptide is conjugated to the (poly) peptide to be modified via the directed and/or the indirect route, said second (poly)peptide is linked to a (pro)drug molecule.

Preferably, said (pro)drug is an anticancer (pro)drug.

In a more preferred embodiment, said anticancer (pro)drug is selected from the group consisting of Etoposide, Phenol mustard, Melphalan, Antifolates (including Methotrexate), Nitrogen mustards, Chloramphenicol, 5-Fluoro-2'-deoxyuridine, Camptothecin, 5-Fluorouracil, 5-Fluorouridine, Anthracycline derivatives, Anthracyclines (including Daunorubicine, Doxorubicin) 9-Aminocamptothecin, Verapamil, Quinine, Dipyridamole, Mitomycin, Vinca Derivatives, Paclitaxel, Docetaxel, Platinum reagents, Benzamide Mustard, Enediynes, Neocarzinostatin, Palytoxin, CC-1065 analogs, Duocarmycin analogs Amino-CBI derivatives, Auristatin, Monomethyl Auristatin, Dolastatatin 10, Maytansine, Maytansinoid DM1, Maytansinoid DM4, Geldanamycin Calicheamicin, therapeutic radioisotopes (yttrium-90 and iodine-131), toxins from bacteria (diptheria toxin or Pseudomonas exotoxin) and toxins from plants (castor bean-derived ricin or gelonin).

It is particularly preferred to employ the method of the invention in those cases where (pro)drugs exhibit high toxicity and/or poor intracellular delivery and/or poor delivery across intracorporal barriers such as the blood brain barrier.

Preferably, said oligonucleotide is selected from the group consisting of antisense oligonucleotides, siRNAs and ribozymes.

As known in the art, antisense RNA sequences are complementary to an mRNA or a part thereof and can selectively bind to said mRNA, said sequence being capable of inhibiting the synthesis of the protein encoded by mRNA. Ribozymes according to the invention are complementary to an mRNA or a part thereof and can selectively bind to and cleave said mRNA, thus inhibiting the synthesis of the proteins encoded by said mRNA. Preferably, the antisense RNA and ribozyme of the invention are complementary to the coding region of the mRNA, e.g. to the 5' part of the coding region. The person skilled in the art, provided with the sequences of the sequence of said mRNA or of a gene encoding said mRNA will be in a position to produce and utilize the above described antisense RNAs or ribozymes. siRNAs are small interfering RNAs to be employed in RNAi technology (see, e.g. Zamore Nat Struct Biol 2001, 8(9):746-50 or Tuschl T. CHEMBIOCHEM. 2001, 2:239-245).

Preferably, said (poly)peptide is an antibody or fragment or derivative thereof retaining the binding specificity of said antibody. An illustration of the method of the invention applied to antibodies is provided in FIG. 3 (direct method) and 4 (indirect method).

The term "antibody or fragment or derivative thereof" according to the invention includes monoclonal antibodies, polyclonal antibodies, single chain antibodies, or fragments thereof and furthermore bispecific antibodies, synthetic antibodies and antibody fragments such as Fab, F(ab$_2$)', Fv or scFv fragments etc., or a chemically modified derivative of any of these. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit.

The term "monoclonal" or "polyclonal antibody" (see Harlow and Lane, (1988), loc. cit.) also relates to derivatives of said antibodies which retain or essentially retain their binding specificity. Other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

The term "binding specificity" in connection with the antibody used in accordance with the present invention means that the antibody etc. does not or essentially does not cross-react with antigens having a structure similar to that of the target antigen. Cross-reactivity of a panel of antibodies etc. under investigation may be tested, for example, by assessing binding of said panel of antibodies etc. under conventional conditions (see, e.g., Harlow and Lane, (1988), loc. cit.) to the antigen of interest as well as to a number of more or less (structurally and/or functionally) closely related antigens. Only those antibodies that bind to the antigen of interest but do not or do not essentially bind to any of the other antigens which are preferably expressed by the same tissue as the antigen of interest, are considered specific for the antigen of interest.

In a particularly preferred embodiment of the method of the invention, said antibody or antibody binding portion is or is derived from a human antibody or a humanized antibody.

The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

In a preferred embodiment of the method of the invention, said crown ether is selected from the group consisting of 18-crown-6,12-crown-4,15-crown-5, benzo-18-crown-6, dibenzo-18-crown-6,12-crown-4,15-crown-5, (12-crown-4)-2-methanol, 18-crown-6 tetracarboxylic acids, (18-crown-6)-2-methanol, benzo-15-crown-5, dibenzo-15-crown-5,4'-amino-benzo-15-crown-5,4'-amino-benzo-18-crown-6 and calixarenes such as calix[4]arene, calix[6]arene, calix[8]arene, and calix[6]arene-hexaacetic acid hexaethylester.

More preferably, said crown ether is 18-crown-6.

The present invention also relates to the use of a crown ether-bound (poly)peptide as an intermediate in the synthesis of a modified (poly)peptide, wherein said (poly)peptide is modified at one or more carboxylic groups by esterification or thioesterification and/or at the amino group of the N-terminal amino acid by amidation or alkylation.

In a preferred embodiment of the use of the invention, said modified (poly)peptide is obtainable by the method of the invention.

The present invention also relates to a modified (poly)peptide obtainable by the method of the invention.

Also embraced by the present invention is a (poly)peptide which is modified with one or more biocompatible polymers, lipids, linkers comprising a hydroxyl group, second (poly)peptides, oligonucleotides, (pro)drugs, markers, labels, molecules of methanol or benzyl alcohol, small molecules having a cognate transport carrier or any combination thereof, wherein said biocompatible polymer, lipid, linker, second (poly)peptide, oligonucleotide, (pro)drug, marker, label or molecules of methanol, benzyl alcohol or small molecules having a cognate transport carrier is/are attached to a (poly)peptide carboxylic group via an ester or thioester bond, and/or which is amidated or alkylated at the amino group of the N-terminal amino acid. Examples of (poly)peptides wherein carboxyl groups are esterified with methanol or benzyl alcohol are provided herein below. Furthermore, esterification may be performed with 4-(2-hydroxyethyl)-2-2-dimethyl-1, 3-dioxolane (see Example 1 (b)) or thioesterification with thioglycerol (see Example 2), respectively.

In a preferred embodiment of the (poly)peptide of the invention, said (poly)peptide carboxylic group is selected from the group consisting of (a) one or more side-chain carboxylic groups of Glu; (b) one or more side-chain carboxylic groups of Asp; (c) the main-chain carboxylic group of the C-terminal amino acid; or (d) any combination of (a) to (c).

In a further preferred embodiment of the (poly)peptide of the invention, said linker carries one or more (a) biocompatible polymers; (b) lipids; (c) linkers; (d) second (poly)peptides; (e) oligonucleotides; (f) (pro)drugs; (g) markers; (h) labels; (i) small molecules having a cognate transport carrier; or any combination of (a) to (i).

Preferably, said biocompatible polymer is selected from the group consisting of polyethers, polysaccharides, polyesters (including polyorthoester), polyalkylcyanoacrylates, hydroxyalkylacrylamides, surfactants and mixtures thereof.

Preferably, said biocompatible polymer is branched and/or cross-linked.

Preferably, the polyether is PEG or the polyester is poly (lactic/glycolic) acid.

Preferably, said second (poly)peptide is a membrane-penetrating (poly)peptide.

In a preferred embodiment of the (poly)peptide of the invention, said second (poly)peptide is linked to a (pro)drug molecule.

Preferably, said (pro)drug is an anticancer (pro)drug.

Preferably, said oligonucleotide is selected from the group consisting of antisense oligonucleotides, siRNAs and ribozymes.

In a preferred embodiment, said (poly)peptide is an antibody or fragment or derivative thereof retaining the binding specificity of said antibody.

Figure 6:
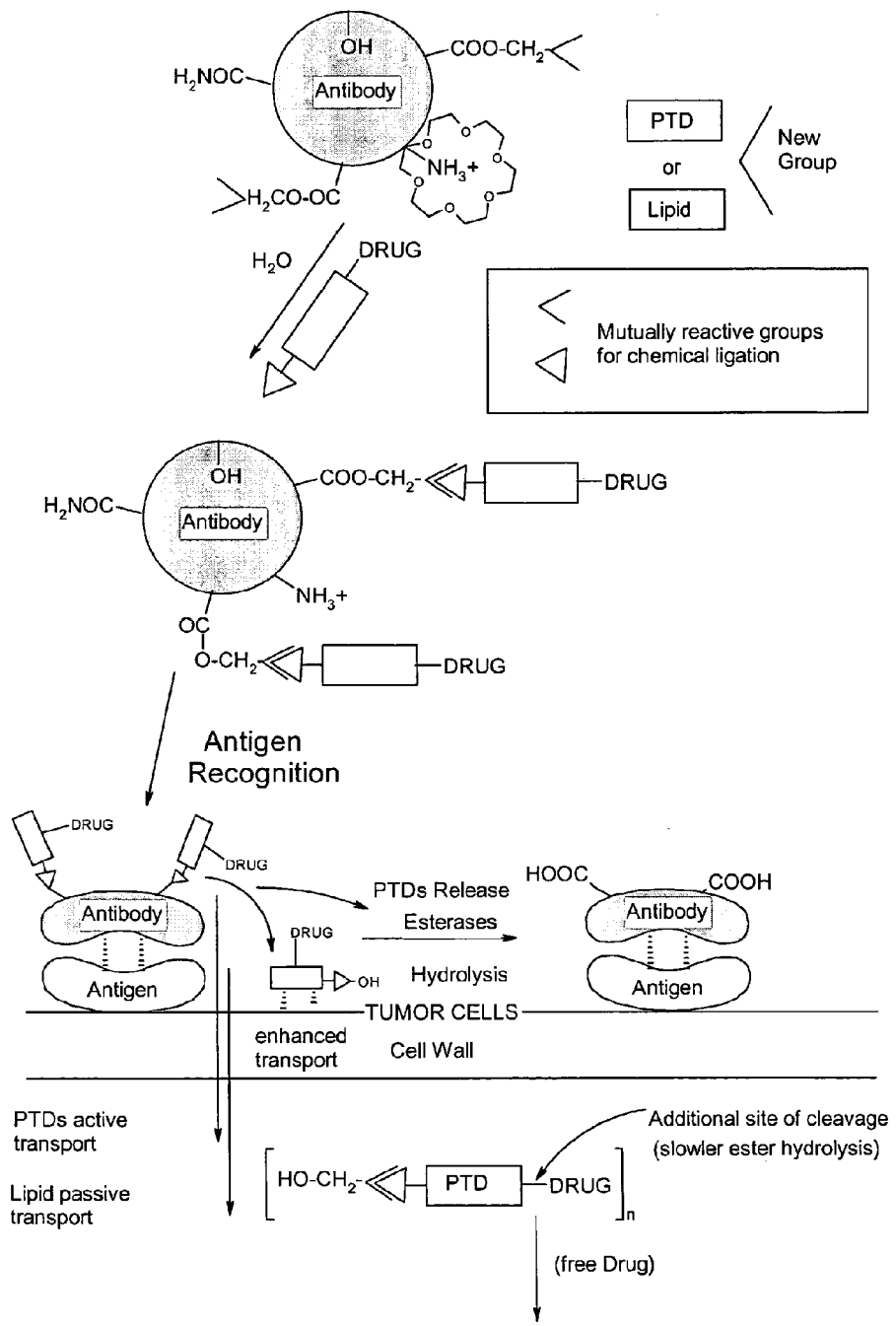

The present invention also relates to an antibody or fragment or derivative thereof retaining the binding specificity of said antibody, carrying one or more linkers attached to one or more carboxylic groups of said antibody or fragment or derivative thereof via an ester or thioester bond, wherein said linker carries a membrane-penetrating (poly)peptide which in turn carries a (pro)drug molecule. This construct according to the invention permits to deliver a drug into a specific cell type. Specificity of delivery is achieved via the binding specificity of the antibody or fragment or derivative thereof which, for example, recognizes a cell surface marker present on one or more cell types to be targeted by the therapeutic intervention. Cleavage of the ester or thioester bond results in the conjugate of membrane-penetrating (poly)peptide and (pro)drug set free. The membrane-penetrating (poly)peptide in turn allows entry into cell and inside the cell, the active compound is cleaved from the membrane-penetrating (poly)peptide, e.g. by intracellular enzymes and, if provided as a prodrug, rendered active. This embodiment of the invention is illustrated in FIG. 6.

The present invention furthermore embraces a pharmaceutical composition comprising the (poly)peptide and/or the antibody or fragment or derivative thereof of the present invention.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of pharmaceutical composition administered to an individual will, inter alia, depend on the nature of the compound. For example, if said compound is a (poly)peptide or protein the total pharmaceutically effective amount of pharmaceutical composition administered parenterally per dose will be in the range of about 1 µg protein/kg/day to 10 mg protein/kg/day of patient body weight, although, as noted above, this will be subject to therapeutic discretion. More preferably, this dose is at least 0.01 mg protein/kg/day, and most preferably for humans between about 0.01 and 1 mg protein/kg/day. If given continuously, the pharmaceutical composition is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988). Sustained release pharmaceutical composition also include liposomally entrapped compound. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The present invention also relates to the use of the (poly) peptide of the invention for the manufacture of a pharmaceutical composition for the treatment of a disease, wherein (a) the (poly)peptide is insulin and the disease is diabetes; (b) the (poly)peptide is EPO and the disease is anemia or chronic renal failure; (c) the (poly)peptide is G-CSF and the disease is neutropenia; (d) the (poly)peptide is an asparaginase and the disease is cancer; (e) the (poly)peptide is Factor VII and the disease is uncontrolled bleeding; (e) the (poly)peptide is interferon α and the disease is chronic hepatitis B or C; (g) the (poly)peptide is interferon γ and the disease is fibrosis, tuberculosis, meningitis or cancer; (h) the (poly)peptide is B2036 and the disease is acromegaly; (i) the (poly)peptide is a superoxide dismutase and the disease is a brain injury; (j) the (poly)peptide is interleukine-2 and the disease is cancer or a condition requiring immunostimulation; (k) the (poly)peptide is hirudine and the disease is heparin-induced thrombocytopenia or angina, and wherein the (poly)peptide is modified as defined herein above. This embodiment relates to the use of (poly)peptides with known biological activity and of established therapeutic relevance, which are modified according to the invention in order to modify, enhance or improve their pharmacological properties. It is understood that the invention also relates to the use of further therapeutically relevant (poly)peptides which are modified according to the invention. In this case, the envisaged medical indication is that indication which can be prevented, ameliorated or cured with the (poly)peptide under consideration.

The human growth hormone (hGH) antagonist B2036 is well known in the art. B2036 is obtained from hGH by the introduction of nine amino acid replacements conferring antagonistic properties and increased receptor affinity (see U.S. Pat. No. 5,849,535). For the purpose of treating acromegaly any other growth hormone (GH)-receptor antagonist (alternatively or in addition to the GH-receptor antagonist B2036) is envisaged. Preferred cancer forms amenable to treatment with asparaginases are lymphoblastic leukemias and large cell lymphoma.

The present invention also relates to the use of a (poly) peptide of the invention, wherein said (poly)peptide is linked to an anticancer (pro)drug for the manufacture of a pharmaceutical composition for the treatment of cancer.

The present invention also relates to the use of the (poly) peptide of the invention which is an antibody, fragment or derivative thereof or of the antibody or fragment or derivative thereof of the invention for the manufacture of a pharmaceutical composition for the treatment of cancer, wherein said (pro)drug is an anticancer (pro)drug and said (poly)peptide or antibody or fragment or derivative thereof specifically binds a tumor-associated antigen. The term "tumor-associated antigen" is well known in the art and designates antigens which are preferentially or virtually exclusively expressed by tumor cells. It is preferred that said tumor-associated antigen is expressed on the surface of the tumor cell.

In a preferred embodiment of said use, said tumor-associated antigen is selected from the group consisting of CD30, CD70, CanAg, CD22, PSMA, CD56, Lewis$^y$ CD33, CD20, CD44v6, CG56972, CD52, HER2/neu, HER2, ErbB2, VEGF, VEGFR2, EGFR, TRAIL-R1 and PEM.

In a more preferred embodiment of the use of the invention, said (poly)peptide or antibody or fragment or derivative thereof specifically binding said specific tumor-associated antigens are to be used for specific forms of cancer. In those cases where said (poly)peptide or antibody or fragment or derivative thereof specifically binds CD30, Hodgkin's or non-Hodgkin lymphoma are to be treated according to this preferred embodiment; similarly CD70 is an antigen presented by cells involved in renal cell carcinoma; CanAg an antigen presented by cells involved in gastrointestinal and non-small cell lung cancer; CD22 in B-cell leukemia; PSMA in prostate cancer; CD56 in small cell lung cancer and neuroendocrine multiple myeloma; Lewis$^y$ in non-small-cell-lung, colon and gastric cancer; CD33 in acute myelogenous leukaemia, PEM in Ovarian cancer, CD44v6 in head, neck and breast cancer, HER2 in breast cancer, GC56972 in melanoma, EGFR and VEGF in metastatic colon cancer, CD52 in chronic lymphocytic leukaemia and CD20 in relapsed/refractory non-Hodgkin lymphoma.

The Figures show:

FIG. 1: Direct (a) and indirect or two-step (b) esterification of (poly)peptide carboxyl groups.

Figure 2:
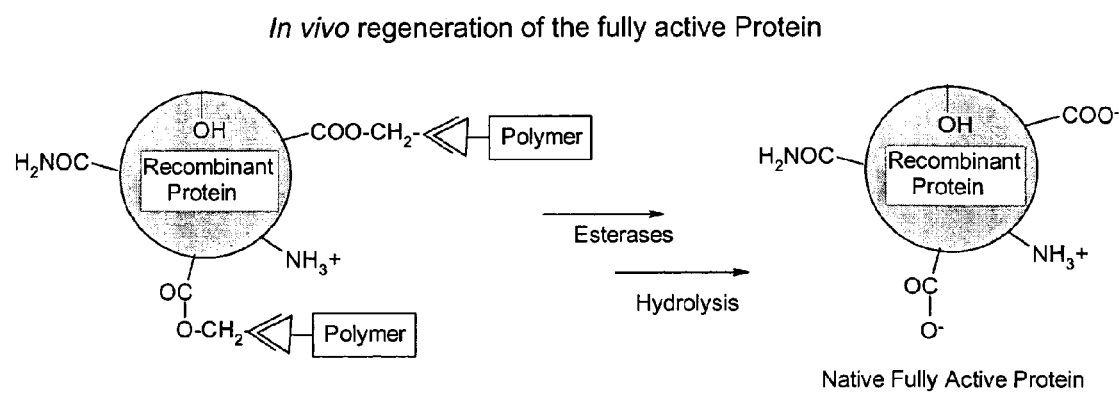

FIG. 2: In vivo reversibility of ester bond formation.

Figure 3:
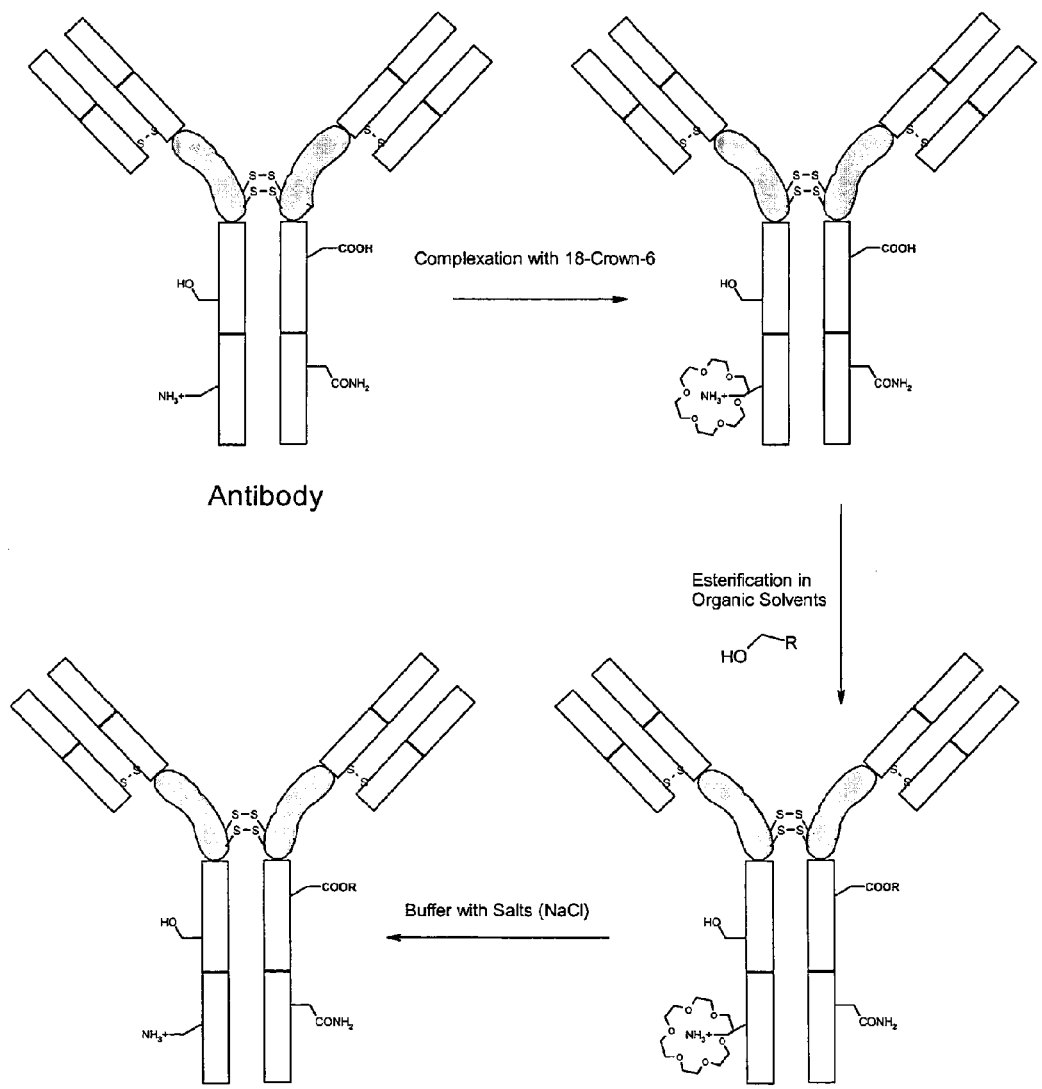

FIG. 3: Direct esterification of antibody carboxyl groups.

Figure 4:
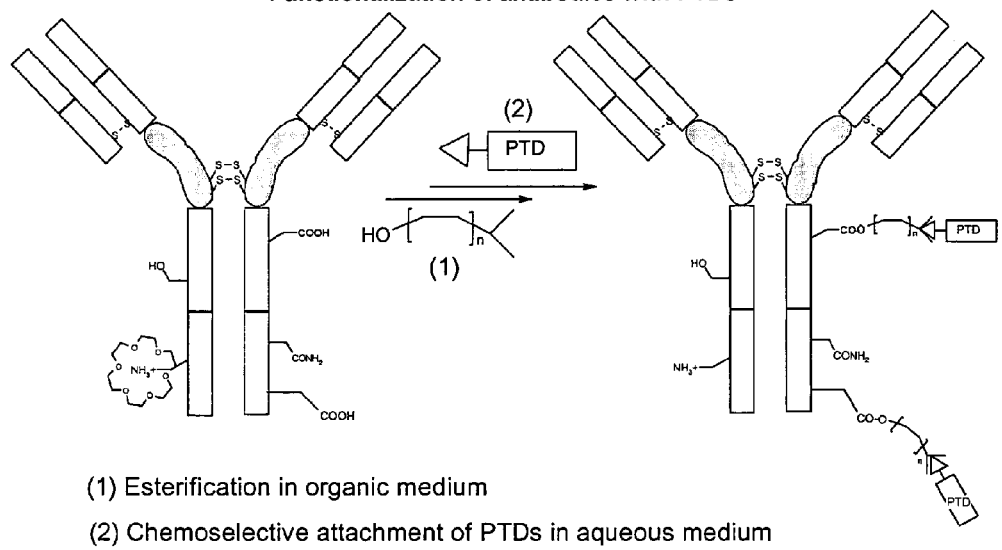

FIG. 4: Two-step modification of antibodies. "PTD" stands for protein transducing domain.

Figure 5:
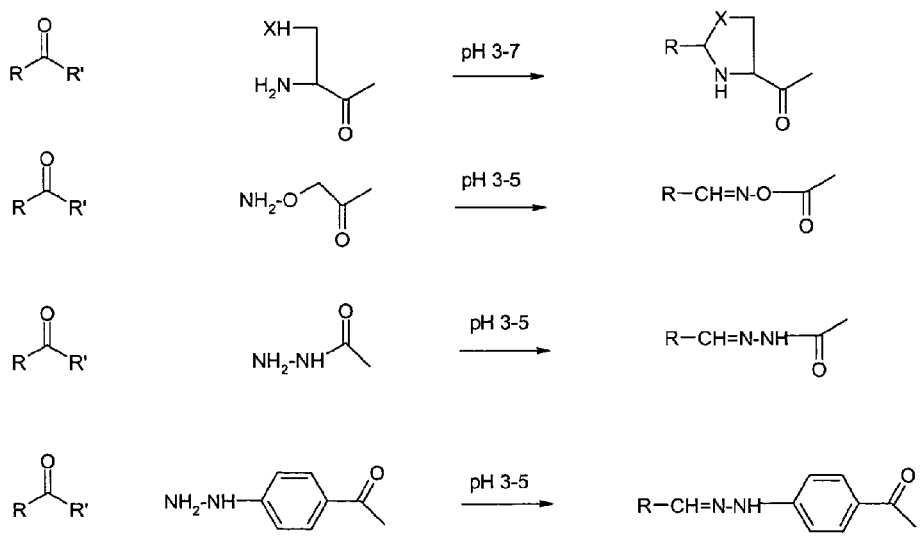
Figure 5:
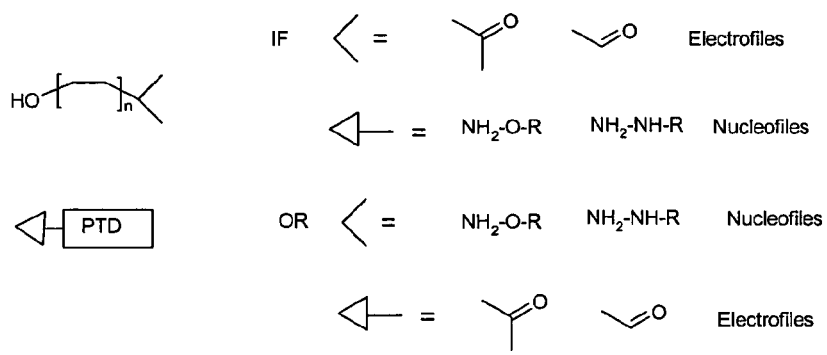

FIG. 5: Exemplary functional groups involved in the second step of the two-step modification of (poly)peptides according to the invention.

FIG. 6: Exemplary antibody—absorption enhancer (lipid or protein-transducing domain)—drug conjugate and its route taken in the human or animal body.

Figure 7:
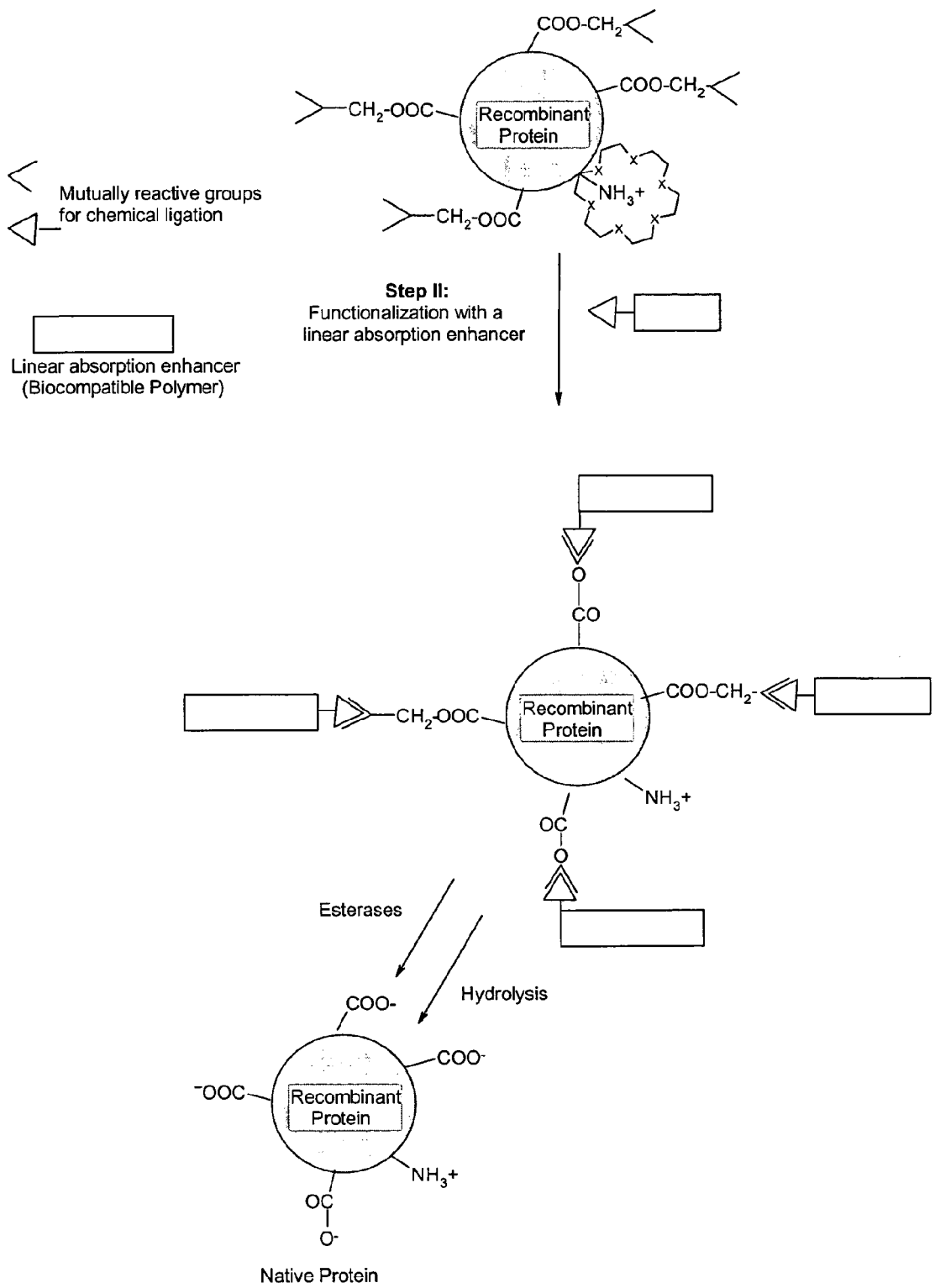

FIG. 7: Modified (poly)peptide exhibiting enhanced absorption/delivery characteristics FIG. 8: Modified (poly)peptide with n (number of copies) of a polymer attached via reversible ester bond to achieve a shielding effect on the surface of the molecule. The shielding of the molecule is obtained by a polymer wrapping with a sufficient number of copies of the polymer.

FIG. 9: Modified (poly)peptide protected from enzymatic digestion by the shielding effect exerted by cross-linked biocompatible polymer molecules attached to the (poly)peptide. The (poly)peptide also exhibits enhanced absorption.

Figure 10:
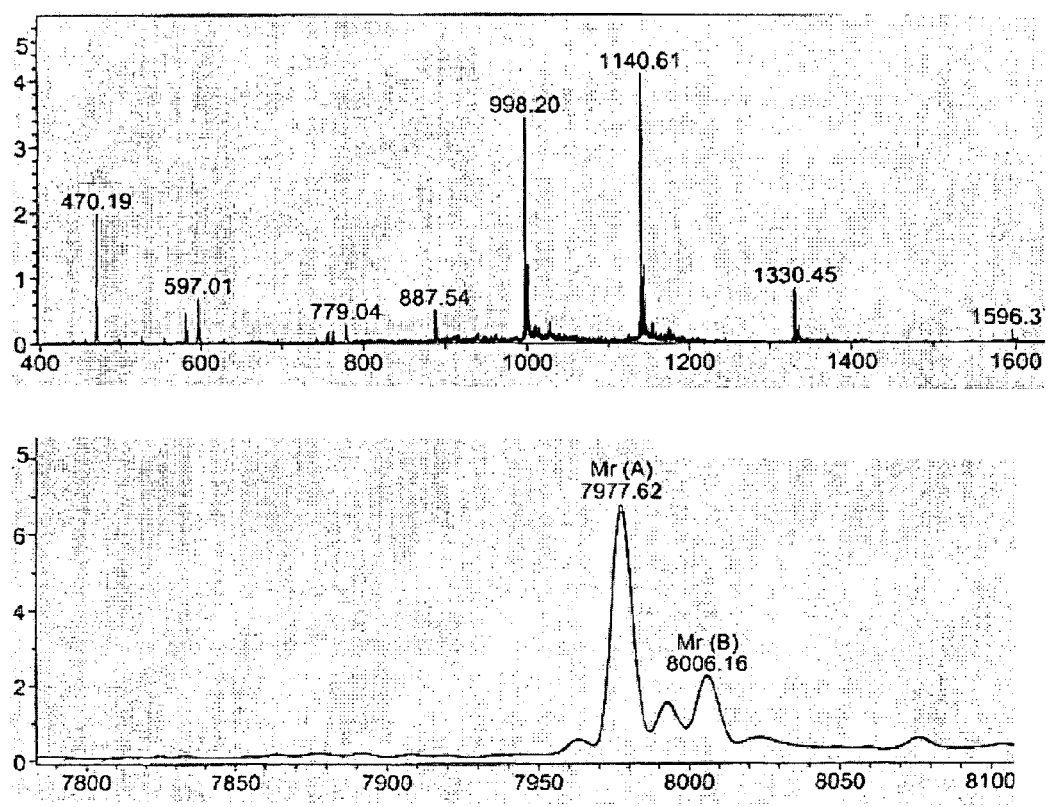

FIG. 10: MS of esterification of [N-formyl-Trp$^{57}$]PSC-Rantes in Methanol.

Figure 11:
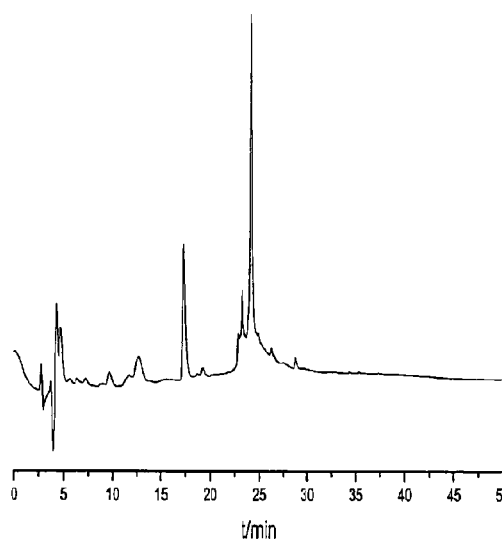
Figure 11:
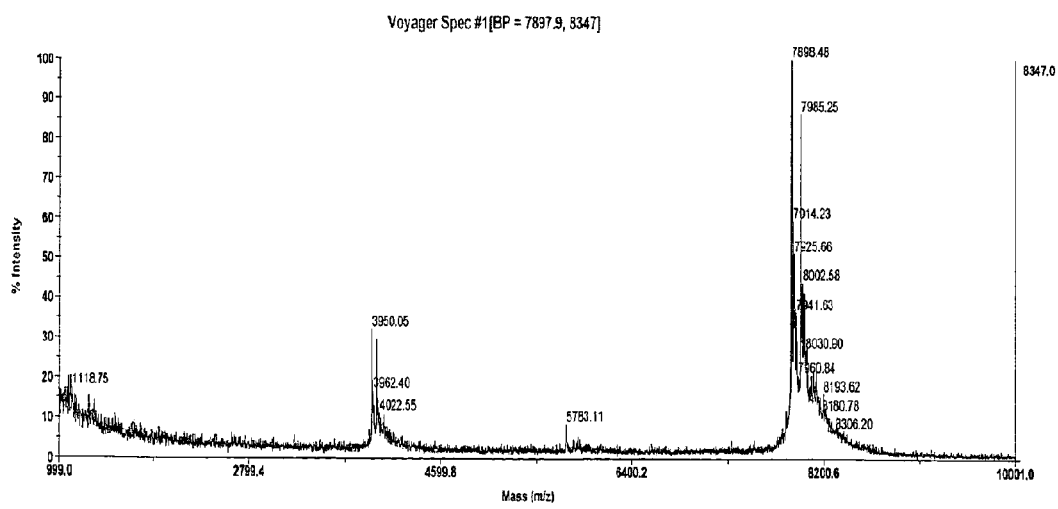

FIG. 11: HPLC (upper part) and MS (lower part) of Esterification of PSC-Rantes with 4-(2-hydroxyethyl)-2-2-dimethyl-1,3-dioxolane FIG. 12: HPLC and MS of M8 thioglycerol esterification: Peak 1 (1 ester formed), Peak 2 (two esters formed)

Figure 14:
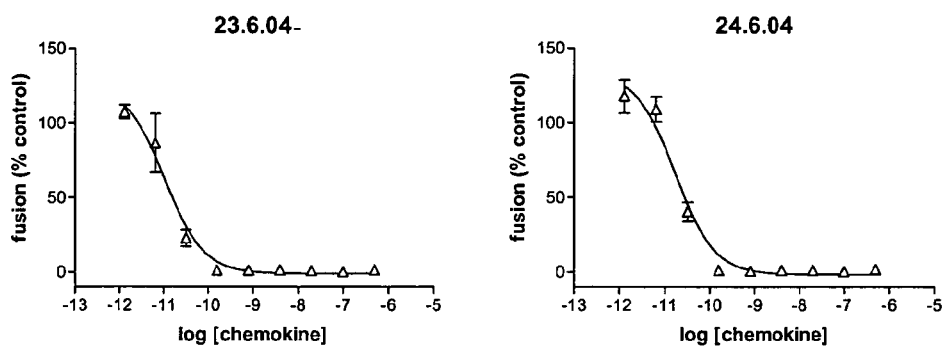
Figure 14:
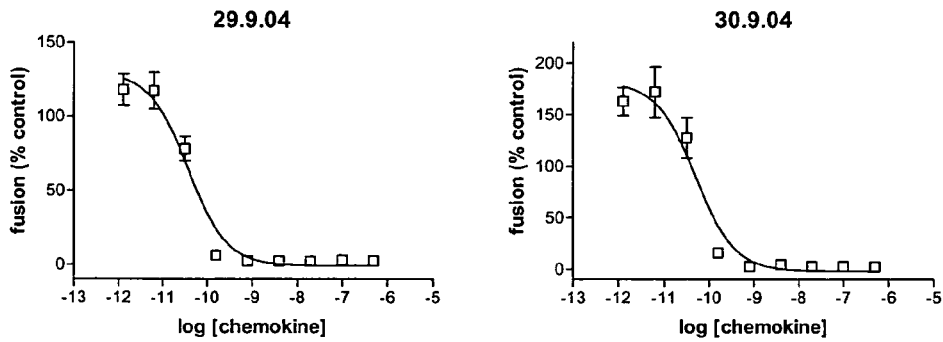

FIG. 13: Exemplary reaction sequence for N-terminal modification of (poly)peptides FIG. 14: Impact of complexation with crown ether on biological activity. (a) Biological assays (in double) of [N-formyl Trp57 PSC-Rantes] for fusion inhibition activity of HIV-1; (b) Biological assays (in double) of [N-formyl Trp57 PSC-Rantes] after complexation with 18-crown-6 and solubilization in methanol. After methanol evaporation and desalting step via filtration on column HPLC, the protein was dissolved in physiological buffer and tested for fusion inhibition activity of HIV-1.

Figure 15:
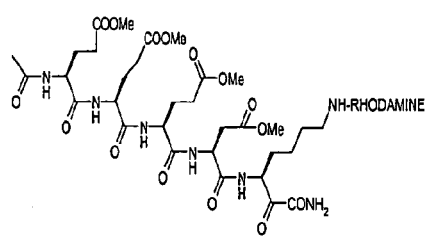
Figure 15:
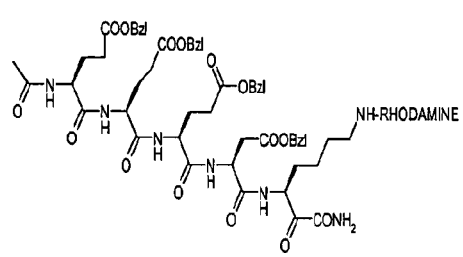
Figure 15:
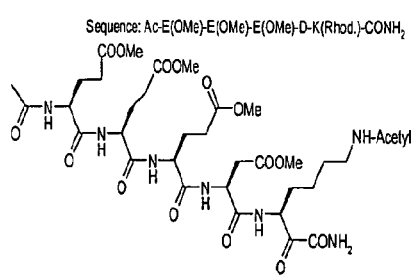
Figure 15:
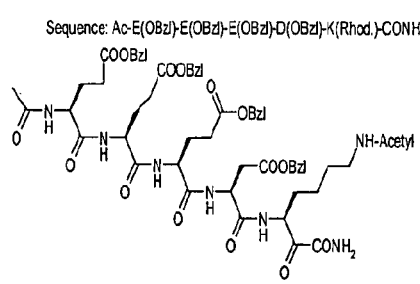
Figure 15:

FIG. 15: (a) Constructs designed to deliver the Ac-EEED peptide into cells through a semi-permanent carboxy esterification strategy. (b) Rat embryonic fibroblasts (REF-52 cells) transfected with the α-SMA-EGFP construct (Clement et al., J Cell Sci. 118, 1395-1404 (2005)) were trypsinized, plated on coverslips for 1 days in DMEM/2% FCS and treated with SMA-Peptide [Ac-E(OBzl)-E(OBzl)-E(OBzl)-D (OBzl)-K(Ac)-CONH$_2$] (5 μg/ml) for 45 min in DMEM without FCS (37 C, incubator). Cells were the rinsed in DMEM, fixed with 1% PFA, and mounted for confocal microscopy (LSM510, Carl Zeiss) observation. α-SMA-EGFP transfected cells were either untreated (control; left), or treated for 45 minutes with SMA-Peptide [Ac-E(OBzl)-E(OBzl)-E (OBzl)-D(OBzl)-K(Ac)-CONH$_2$] (right). SMA-FP treatment provokes α-SMA positive-stress fiber disappearance.

Figure 16:
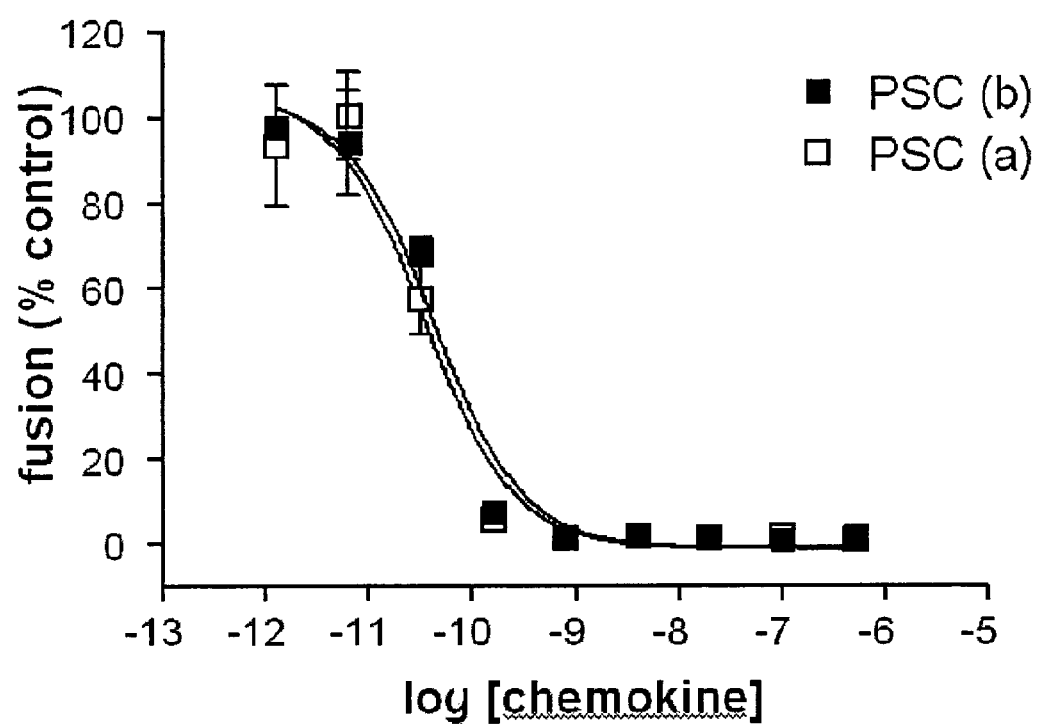

FIG. 16: Impact of complexation with crown ether in organic solvents on biological activity. (a) Biological assays of the chemokine PSC-Rantes for fusion inhibition activity of HIV-1; (b) Biological assays of PSC-Rantes after complexation with 18-crown-6 and solubilization in methanol for 6 hrs. After methanol evaporation and desalting step, the protein was dissolved in physiological buffer and tested for fusion inhibition activity of HIV-1.

Figure 17:
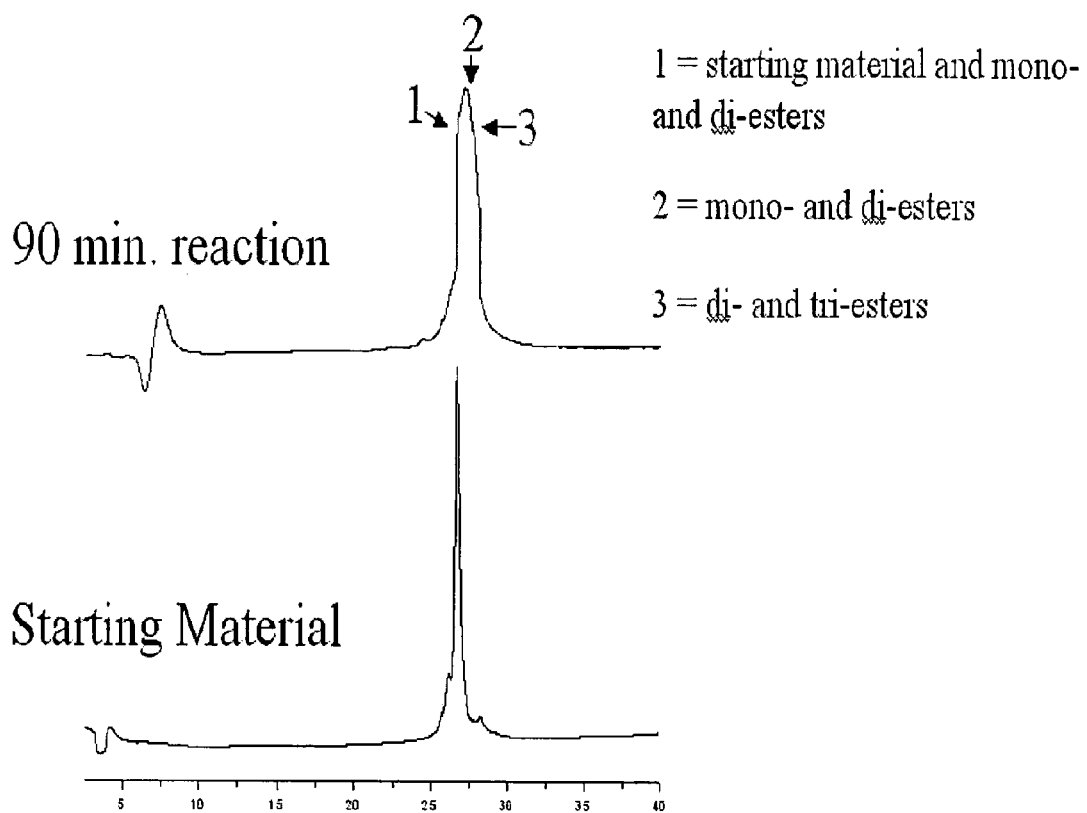
Figure 17:
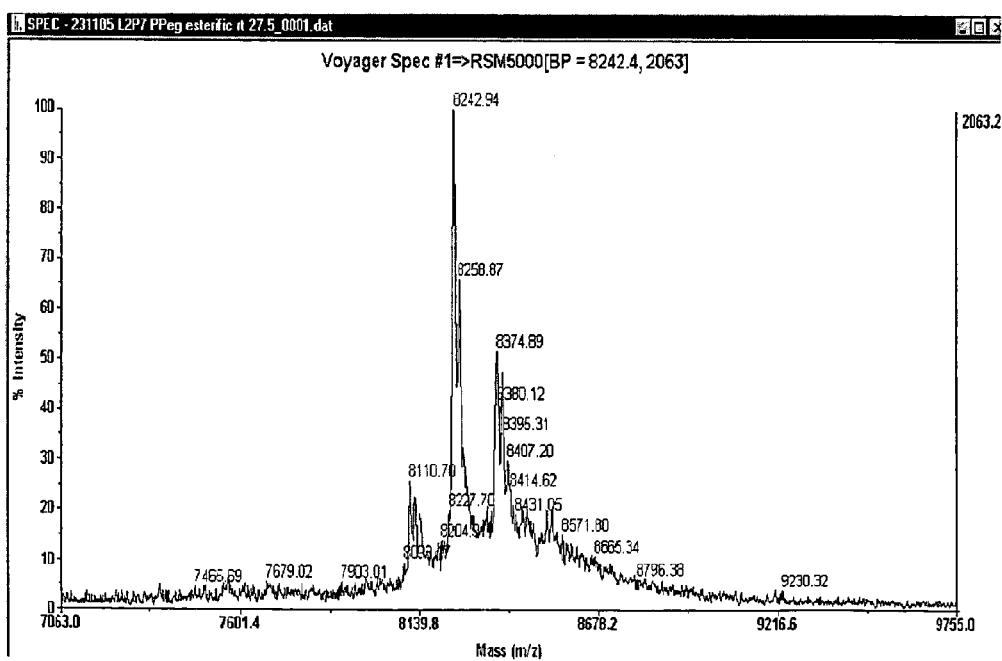

FIG. 17: Results of esterification of a chemokine called L2P7 of sequence FAPMSQQSTSCCFAYIARPLPRA-HIKEYFYTSGKCSNPAVVFVTRKNRQVCANPE KKWVREYINSLEMS with a short PEG (HOCH$_2$CH$_2$(OCH$_2$CH$_2$)$_2$OH). HPLC traces (top) and MS spectrum (bottom).

The following examples illustrate the invention but should not be construed as being limiting.

EXAMPLE 1

Esterification Experiments Using Folded PSC-Rantes (a) Methyl-Ester Formation.

[N-formyl-Trp$^{57}$]PSC-Rantes 0.5 mg, (MW=7921) was complexed with 2.5 mg of 18-crown-6 in a mixture of DCM/Methanol. Then the solvent was evaporated and the residue was taken up in 0.2 ml of methanol. Then 11 µl of chlorotrimethyl silane were added and followed by reaction for 1 h at room temperature. The mass spectrum of the major peak shows a major product consistent with 4 esters formed (MW=7977) and traces of 5 esters (MW=7991) and 6 esters (MW=8006) (see FIG. 10).

As control, a sample of the formyl-Trp derivative of PSC-Rantes was complexed with 18-crown-6 as described above. Then the sample was dissolved in methanol as described above and left at room temperature for 1 h. The methanol was evaporated, and the protein was desalted via HPLC to remove the 18-crown-6. The protein was tested for fusion inhibition activity of HIV-1 in an R5-tropic envelope-dependent cell fusion assay (Hartley, O. et al., Proc. Natl. Acad. Sci. USA 101, 16460-16465 (2004)) and found as potent as a reference sample, thereby proving that the complexation and solubilization of the protein with crown ethers has not caused any loss of biological activity (see FIGS. 14 and 16).

(b) 4-(2-hydroxyethyl)-2-2-dimethyl-1,3-dioxolane (MW 146.18) ester formation.

PSC-Rantes 0.5 mg, (MW=7894) was complex with 2.5 mg of 18-crown 6 in a mixture of DCM/Methanol. Then the solvent was evaporated and the residue was taken up in 0.2 ml of 4-(2-hydroxyethyl)-2-2-dimethyl-1,3-dioxolane. Then 11 µl of chlorotrimethyl silane were added followed by reaction for 45 minutes at room temperature. After 1 h, the major peak by HPLC (FIG. 11, upper part) showed approximately 50% of 1 ester formation. Notably, the dioxolane ring opened and the MS of the product is consistent with the lost of one molecule of acetone. Such effect is presumably due to the hydrolysis (with traces of water) of the cyclic structure by the HCl generated from chlorotrimethylsilane (acidic conditions). The corresponding MS spectrum is shown in FIG. 11, lower part.

EXAMPLE 2

Chemokine M8 Esterification

Figure 12:
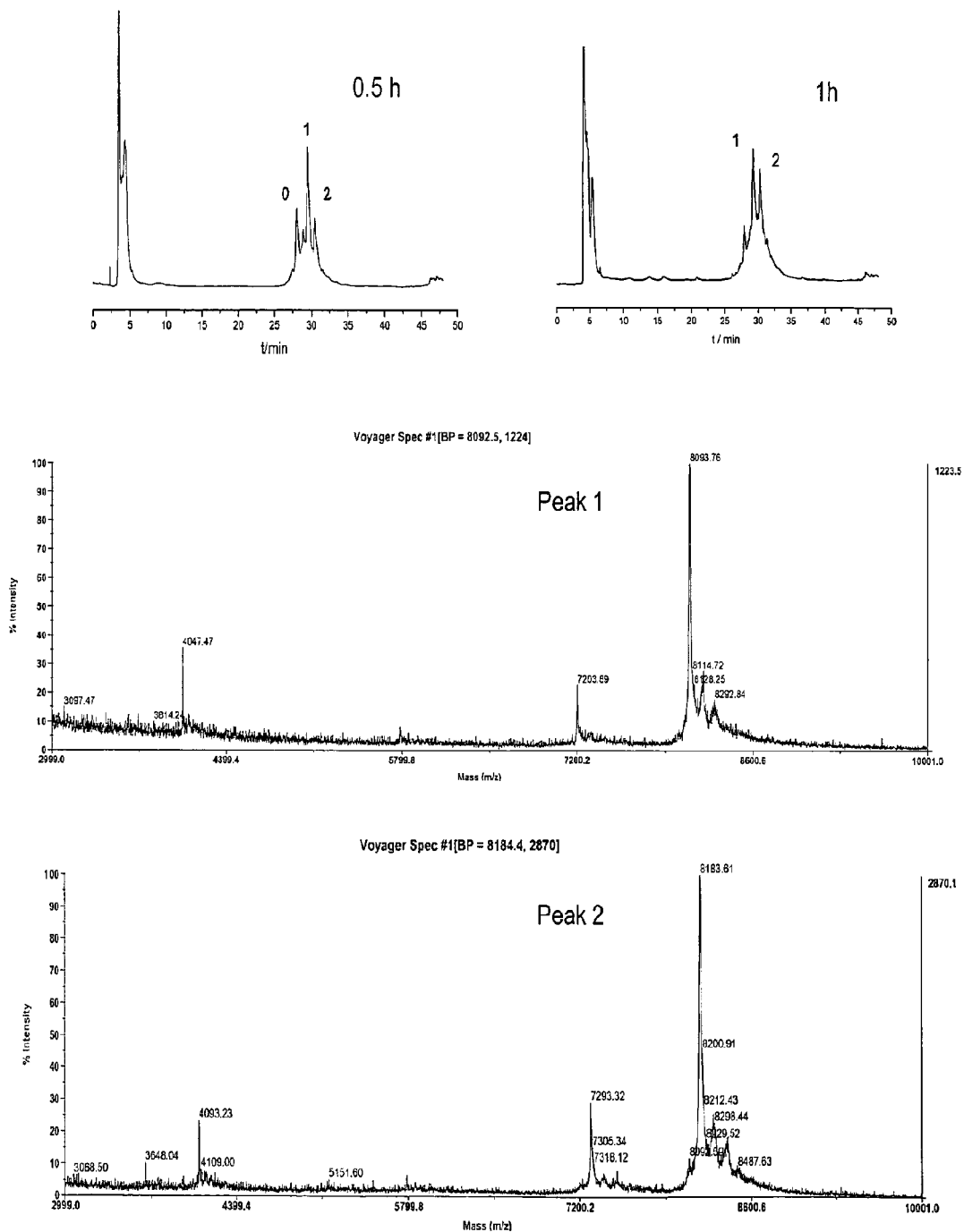

Thioglycerol (Mw 108.1) ester formation has been performed with a new chemokine obtained by phage display called M8 and donated by Dr. Oliver Hartley. The chemokine M8 0.25 mg, (MW=7995.3) was complex with 18-crown-6 as described before. the solvent was evaporated and the residue was taken up in 0.1 ml of anhydrous thioglycerol. Then 5 µl of chlorotrimethyl silane were added and followed by reaction for 30 and 60 minutes at room temperature. The corresponding HPLC data and MS spectra are shown in FIG. 12.

EXAMPLE 3

Esterification of a Model Chemokine L2P7

Folded chemokine L2P7 of Ms 7976.5, 0.2 mg complex with 18-crown-6 was dissolved in 0.1M of the commercially available PEG (HOCH$_2$CH$_2$(OCH$_2$CH$_2$)$_2$OH). Then, 8 µl of chlorotrimethyl silane were added and followed by reaction for 30 and 90 minutes at room temperature. The corresponding HPLC data and MS spectra are shown in FIG. 17 at t=90 minutes. MALDI MS shows peaks of Ms 8242.94 corresponding to adducts with 2 PEG molecules and 8374.89 corresponding to adducts with 3 PEG molecules.

EXAMPLE 4

Cell-Penetrating Properties of an Esterified Peptide

Ac-EEED is a short peptide which has been shown in studies using both microinjection (Chaponnier et al. JCB, 1995) and fusion to a PTD (Hinz et al. JCB, 2002), to be capable of blocking polymerisation of α-smooth muscle-actin (α-SMA) and hence regulating the formation of stress fibres, which are involved in a number of physiological processes, most notably myofibroblast contractile activity during wound healing. This example relates to delivery of the peptide using a semi-permanent carboxy esterification strategy of a synthetic peptide incorporating a C-terminal lysine residue, whose carboxy terminus is amidated and whose epsilon amino group is either acetylated or used as a handle to attach a tracer (fluorochrome, biotin, etc, FIG. 15(a)). Four constructs have been tested, varying the lipophilicity of the protecting ester moiety. The template with the carboxylates esterified with benzyl groups showed penetration into the cell monitored by detection of the expected biological activity (FIG. 15(b)).

Even if the extent of the penetration (measured by comparison with the biological activity of standards) was incomplete, this could be easily explained by the poor solubility in water of our template and or by a non quantitative cleavage of every ester moiety in each molecule. Thus, introduction for example of a Polyethylenglycol (PEG) chain on the side chain of lysine as replacement for the acetyl group or at the C$^α$ will favour at the same time aqueous partitioning of the molecule and solvatation of the esters group, solving both problems at once.

FURTHER REFERENCES

Botti, P. et al., *J. Pept. Sci.* 2, 371-380 (1996).
Julian et al., *Int. J. Mass Spectrom.* 210, 613 (2001).
Oshima, T. et al., *Biomacromolecules* 3, 438-444 (2002).
Roberts, M. J. et al., *Adv. Drug Deliv. Rev.* 54, 459-476 (2002).
Tsubery et al., *J. Biol. Chem.* 279, 38118-38124 (2004).
Yamada, T. et al., *Inorg. Chem.* 39, 3049-3056 (2000).

The invention claimed is:

1. A method of producing a modified (poly)peptide, comprising: modifying in an organic solvent a crown ether-bound (poly)peptide at one or more carboxylic groups by esterification or thioesterification and/or at the amino group of the N-terminal amino acid by amidation or alkylation, wherein the modifying by an ester or thioester bond is selected from the group consisting of the formation of (an) ester or thioester bond(s) with one or more (a) biocompatible polymers; (b) lipids; (c) linker molecules comprising a hydroxyl group or sulfhydryl group; (d) side-chain hydroxyl groups of said (poly)peptide; (e) oligonucleotides; (f) (pro)drugs; (g) markers; (h) labels; (i) small molecules having a cognate transport carrier; and any combination of (a) to (i).

2. The method of claim 1, wherein said carboxylic group is selected from the group consisting of (a) one or more side-chain carboxylic groups of Glu; (b) one or more side-chain carboxylic groups of Asp; (c) the main-chain carboxylic group of the C-terminal amino acid; and (d) any combination of (a) to (c).

3. The method of claim 1, wherein said method further comprises reacting said linker with a molecule selected from the group consisting of one or more (a) biocompatible polymers; (b) lipids; (c) linkers; (d) second (poly)peptides; (e) oligonucleotides; (f) (pro)drugs; (g) markers; (h) labels; (i) small molecules having a cognate transport carrier; and any combination of (a) to (i).

4. The method of claim 3, wherein said reacting is effected in aqueous medium.

5. The method of claim 1, wherein said biocompatible polymer is selected from the group consisting of polyethers, polysaccharides, polyesters, polyorthoesters, polyalkylcyanoacrylates, hydroxyalkylacrylamides, surfactants and mixtures thereof.

6. The method of claim 1, wherein said biocompatible polymer is branched and/or cross-linked.

7. The method of claim 5, wherein the polyether is PEG or the polyester is poly(lactic/glycolic) acid.

8. The method of claim 3, wherein said second (poly)peptide is a membrane-penetrating (poly)peptide or a (poly)peptide recognized and transported by gastro-intestinal (GI) transport carriers.

9. The method of claim 3, wherein said second (poly)peptide is linked to a (pro)drug molecule.

10. The method of claim 1, wherein said (pro)drug is an anticancer (pro)drug.

11. The method of claim 1, wherein said oligonucleotide is selected from the group consisting of antisense oligonucleotides, siRNAs and ribozymes.

12. The method of claim 1, wherein said (poly)peptide is an antibody or fragment or derivative thereof retaining the binding specificity of said antibody.

13. The method of claim 1, wherein said crown ether is selected from the group consisting of 18-crown-6,12-crown-4,15-crown-5, benzo-18-crown-6, dibenzo-18-crown-6,12-crown-4,15-crown-5, (12-crown-4)-2-methanol, 18-crown-6 tetracarboxylic acids, (18-crown-6)-2-methanol, benzo-15-crown-5, dibenzo-15-crown-5,4'-amino-benzo-15-crown-5, 4'-amino-benzo-18-crown-6, calix[4]arene, calix[6]arene, calix[8]arene, and calix[6]arene-hexaacetic acid hexaethylester.

14. The method of claim 1, wherein said crown ether is 18-crown-6.

* * * * *